United States Patent
Sekiguchi et al.

(10) Patent No.: US 10,997,775 B2
(45) Date of Patent: May 4, 2021

(54) IMAGE PROCESSING APPARATUS, IMAGE PROCESSING METHOD, AND IMAGE PROCESSING SYSTEM

(71) Applicant: CANON KABUSHIKI KAISHA, Tokyo (JP)

(72) Inventors: Hiroyuki Sekiguchi, Kyoto (JP); Kohtaro Umezawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/282,467

(22) Filed: Feb. 22, 2019

(65) Prior Publication Data
US 2019/0188898 A1 Jun. 20, 2019

Related U.S. Application Data

(63) Continuation of application No. PCT/JP2017/031242, filed on Aug. 30, 2017.

(30) Foreign Application Priority Data

Aug. 30, 2016 (JP) .............................. JP2016-167790

(51) Int. Cl.
*G06T 15/08* (2011.01)
*A61B 6/03* (2006.01)
*G06T 1/00* (2006.01)
*G06T 3/40* (2006.01)
*G06T 5/00* (2006.01)
*G06T 5/40* (2006.01)

(52) U.S. Cl.
CPC .............. *G06T 15/08* (2013.01); *A61B 6/03* (2013.01); *G06T 1/00* (2013.01); *G06T 3/4007* (2013.01); *G06T 5/009* (2013.01); *G06T 5/40* (2013.01)

(58) Field of Classification Search
None
See application file for complete search history.

(56) References Cited

U.S. PATENT DOCUMENTS

| | | | |
|---|---|---|---|
| 5,566,282 A | * | 10/1996 | Zuiderveld ............ G06T 15/08 345/424 |
| 7,298,372 B2 | | 11/2007 | Pfister et al. |
| 8,452,066 B2 | | 5/2013 | Oikawa |
| 9,589,391 B2 | | 3/2017 | Sakuragi |

(Continued)

FOREIGN PATENT DOCUMENTS

| | | |
|---|---|---|
| JP | 2001-236492 A | 8/2001 |
| JP | 2002-245487 A | 8/2002 |

(Continued)

OTHER PUBLICATIONS

Zhang, E. Z., et al. "In vivo high-resolution 3D photoacoustic imaging of superficial vascular anatomy." Physics in Medicine & Biology 54.4 (2009): 1035.*

(Continued)

*Primary Examiner* — Ryan M Gray
(74) *Attorney, Agent, or Firm* — Venable LLP

(57) ABSTRACT

The disclosure proposes an image processing apparatus for rendering a maximum intensity projection image by extracting, as objects to be rendered, only voxels having a high brightness value in three-dimensional volume data and using the brightness values of these voxels for the corresponding pixels.

19 Claims, 16 Drawing Sheets

(56) References Cited

U.S. PATENT DOCUMENTS

| | | | |
|---|---|---|---|
| 2006/0077204 A1* | 4/2006 | Pfister | G06T 15/08 345/424 |
| 2009/0096787 A1* | 4/2009 | Masumoto | G06T 15/08 345/424 |
| 2009/0097722 A1* | 4/2009 | Dekel | G06T 7/30 382/128 |
| 2011/0019890 A1 | 1/2011 | Oikawa | |
| 2012/0280994 A1* | 11/2012 | Buyanovskiy | G06T 15/06 345/424 |
| 2013/0177229 A1* | 7/2013 | Inoue | A61B 8/483 382/131 |
| 2013/0222383 A1* | 8/2013 | Taniguchi | A61B 6/466 345/424 |
| 2013/0249913 A1* | 9/2013 | Smout | G06T 15/08 345/424 |
| 2013/0274585 A1* | 10/2013 | Wanda | A61B 5/0091 600/407 |
| 2015/0146954 A1* | 5/2015 | Hatanaka | G06K 9/4647 382/131 |
| 2015/0235369 A1* | 8/2015 | Ishida | A61B 5/0033 382/131 |
| 2015/0279120 A1 | 10/2015 | Sakuragi | |
| 2015/0297187 A1* | 10/2015 | Inoue | A61B 8/5238 600/438 |
| 2016/0155259 A1* | 6/2016 | Lee | G06T 15/08 345/424 |
| 2017/0316588 A1* | 11/2017 | Homann | G06T 11/008 |
| 2020/0077968 A1* | 3/2020 | Benishti | A61B 6/503 |

FOREIGN PATENT DOCUMENTS

| | | | |
|---|---|---|---|
| JP | 2006-107518 A | 4/2006 | |
| JP | 2007-135843 A | 6/2007 | |
| JP | 2009-189489 A | 8/2009 | |
| JP | 2010-152609 A | 7/2010 | |
| JP | 2014-151002 A | 8/2014 | |
| JP | 2015-188574 A | 11/2015 | |
| WO | 2016/110928 A1 | 7/2016 | |

OTHER PUBLICATIONS

Drebin, Robert A., Loren Carpenter, and Pat Hanrahan. "vol. rendering." ACM Siggraph Computer Graphics 22.4 (1988): 65-74.*

Feb. 7, 2020 European Search Report in European Patent Appln. No. 17846598.5.

Lukas Mroz, et al., "Real-time Maximum Intensity Projection," Data Visualization '99, Proceedings of the Joint Eurographics and IEEE TCVG Symposium on Visualization Springer-Verlag/Wien, Austria, 1999, pp. 135-144.

Balázs Csebfalvi, et al., "Fast Visualization of Object Contours by Non-Photorealistic Volume Rendering," Computer Graphics Forum, Wiley-Blackwell Publishing Ltd, GB, vol. 20, No. 3, Jan. 2001, pp. 1-9.

Lukas Mroz, et al., "Interactive High-Quality Maximum Intensity Projection," Computer Graphics Forum Blackwell Publishers for Eurographics Assoc., UK, vol. 19, No. 3, 2000, pp. C341-C350.

Anonymous, "Understanding image-interpolation techniques," Vision Systems Design, Oct. 2007, pp. 1-25.

Mar. 5, 2019 International Preliminary Report on Patentability in International Patent Appln. No. PCT/JP2017/031242.

Nov. 21, 2017 International Search Report in International Patent Appln. No. PCT/JP2017/031242.

* cited by examiner

① PIXEL IS DESIGNATED
② VOXEL ROW IS SPECIFIED
③ MAXIMUM BRIGHTNESS VALUE IN VOXEL ROW IS RETRIEVED
④ DISCOVERED MAXIMUM BRIGHTNESS VALUE IS DISPLAYED
   AS BRIGHTNESS VALUE OF PIXEL

COMPARATIVE EXAMPLE

COMPARATIVE EXAMPLE

① PIXEL IS DESIGNATED
② VOXEL ROW IS SPECIFIED (CONVERSION TO COORDINATE VALUES OF VOXELS CONSTITUTING VOXEL ROW)
③ MAXIMUM BRIGHTNESS VALUE IN VOXEL ROW IS RETRIEVED
④ DISCOVERED MAXIMUM BRIGHTNESS VALUE IS DISPLAYED AS BRIGHTNESS VALUE OF PIXEL

COMPARATIVE EXAMPLE

COMPARATIVE EXAMPLE

COMPARATIVE EXAMPLE

FIG.8

| MSB | | | | LSB |
|---|---|---|---|---|
| z | y | x | value 1 | |
| z | y | x | value 1 | |

133

| UPPER 10% IS USED | UPPER 5% IS USED | UPPER 2.5% IS USED | UPPER 1.25% IS USED |
|---|---|---|---|
|  |  |  |  |
| 0.56 SEC | 0.31 SEC | 0.18 SEC | 0.12 SEC |

* TIME OF SINGLE-CORE PROCESSING FOR ARRANGEMENT OF CONDITIONS IS DISPLAYED

BRIGHTNESS LEVEL IS INCREASED IN DISPLAY BY 50 TO SEE DIFFERENCE (a)            (b)

(a)

(b)

IMAGE PROCESSING APPARATUS, IMAGE PROCESSING METHOD, AND IMAGE PROCESSING SYSTEM

CROSS-REFERENCE TO RELATED APPLICATIONS

This application is a Continuation of International Patent Application No. PCT/JP2017/031242, filed Aug. 30, 2017, which claims the benefit of Japanese Patent Application No. 2016-167790, filed Aug. 30, 2016, both of which are hereby incorporated by reference herein in their entirety.

BACKGROUND OF THE INVENTION

Field of the Invention

The present invention relates to an image processing apparatus that performs movement, enlargement, reduction, rotation display or the like of an image rendered by a maximum intensity projection (MW) method.

Background Art

A maximum intensity projection method is one of three-dimensional image processing methods. In the maximum intensity projection method, a maximum brightness value of picture elements group in a three-dimensional space that are arranged in a direction orthogonal to each pixel on a projection plane is displayed as a brightness value of each pixel on the projection plane. FIG. 1 shows an overview of processing of the maximum intensity projection method which is generally used.

Here, a data space 1 is a three-dimensional space in which volumetric picture element units (hereinafter referred to as "voxels") 2 are arranged in respective directions of an x direction, an y direction, and a z direction and in which a three dimensional image to be projected is defined. Meanwhile, a projection plane 3 is a two-dimensional space in which planar unit picture elements (hereinafter referred to as "pixels") 4 are arranged in respective directions of an X direction and an Y direction and in which the projection image of the abovementioned three dimensional image is formed. Here, the projection image is a maximum intensity projection image.

FIG. 1 shows a case where the projection plane 3 is parallel to the xy plane of the data space 1. In the general maximum intensity projection method, first, the pixel 4 is designated on the projection plane 3, then a row of voxels 2 (a set of N voxels aligned in the z direction) having the same coordinate value as the pixel 4 is specified, and the maximum brightness value among the N voxels 2 is displayed as the brightness value of the designated pixel 4.

FIG. 2 shows an example of a maximum intensity projection image in the case where photoacoustic imaging data are used as the data space 1. The photoacoustic imaging data here are constituted by 1024×1024×200 voxels. In general brightness data, only the brightness data are stored in the memory in order of (0, 0, 0), (1, 0, 0), (2, 0, 0) . . . (1023, 0, 0), (0, 1, 0), (1, 1, 0) . . . (1023, 1, 0), (0, 2, 0) . . . (1023, 1023, 0), (0, 0, 1) . . . (1023, 1023, 200) in the (x, y, z) coordinate system. In this space structure, the time until the creation of the maximum intensity projection image in the z-axis direction, y-axis direction, and x-axis direction is measured. Accordingly, when using a single-core PC, data positions on the memory are separated from the x-axis direction, y-axis direction, and z-axis direction, and due to limitation of cache capacity, 2.15 sec are needed for scanning in the x direction, 2.44 sec are needed for scanning in the y direction and 5.25 sec are needed for scanning in the z direction.

When a rotation display of the maximum intensity projection image displayed on the projection plane 3 is instructed by the user, a positional relationship is changed to such that the projection plane 3 and the xy plane of the data space 1 intersect at an arbitrary angle. FIG. 3 shows a case where the projection plane 3 is not parallel to the xy plane of the data space 1. In this case, in order to specify a row of voxels 2 corresponding to the pixel 4 on the projection plane 3, computational processing (coordinate conversion processing) for obtaining the coordinate values of the corresponding voxel 2 needs to be performed on the basis of the coordinate values of the pixel 4.

CITATION LIST

Patent Literature

PTL 1: Japanese Patent Laid-Open No. 2001-236492
PTL 2: Japanese Patent Laid-Open No. 2009-189489
PTL 3: Japanese Patent Laid-Open No. 2010-152609

SUMMARY OF THE INVENTION

There is proposed an image processing apparatus comprising: a voxel coordinate data generation unit configured to generate voxel coordinate data in which respective brightness values are associated with coordinate values of respective voxels; and a coordinate conversion unit configured to converts the coordinate values to coordinate values of corresponding pixels on a projection plane at least with respect to voxels having a brightness value higher than a predetermined threshold value, or with respect to a predetermined number of voxels in order from a voxel having a largest brightness value, and to display brightness values of the corresponding voxels for the coordinate values of the pixels obtained by the conversion.

There is proposed an image processing apparatus comprising: a voxel coordinate data generation unit configured to generate voxel coordinate data in which coordinate values of one or a plurality of voxels having a brightness value of the same magnitude are associated with each brightness value; and a coordinate conversion unit configured to convert the coordinate values to coordinate values of corresponding pixels on a projection plane at least with respect to voxels having a brightness value higher than a predetermined threshold value, or with respect to a predetermined number of voxels in order from a voxel having a largest brightness value, and to display brightness values of the corresponding voxels for the coordinate values of the pixels obtained by the conversion.

There is proposed an image processing method comprising: a voxel coordinate data generation step of generating voxel coordinate data in which respective brightness values are associated with coordinate values of respective voxels; a coordinate value conversion step of converting the coordinate values to coordinate values of corresponding pixels on a projection plane at least with respect to voxels having a brightness value higher than a predetermined threshold value, or with respect to a predetermined number of voxels in order from a voxel having a largest brightness value; and a brightness display step of displaying a brightness value of the corresponding voxel for the coordinate values of the pixel obtained by the conversion.

There is proposed an image processing program that causes a computer of an image processing apparatus for rendering a projection image based on three-dimensional volume data on a display unit to execute a voxel coordinate data generation step of generating voxel coordinate data in which respective brightness values are associated with coordinate values of respective voxels constituting the three-dimensional volume data; a coordinate value conversion step of converting the coordinate values to coordinate values of corresponding pixels on a projection plane at least with respect to voxels having a brightness value higher than a predetermined threshold value, or with respect to a predetermined number of voxels in order from a voxel having a largest brightness value; and a brightness display step of displaying a brightness value of the corresponding voxel for the coordinate values of the pixel obtained by the conversion.

There is proposed an image processing system for rendering a projection image based on three-dimensional volume data on a display unit, the image processing system comprising a server that stores the three-dimensional volume data, an image processing apparatus, and a network that connects the server and the image processing apparatus, wherein the image processing apparatus includes a voxel coordinate data generation unit configured to generate voxel coordinate data in which respective brightness values are associated with coordinate values of respective voxels constituting the three-dimensional volume data; and a coordinate conversion unit configured to convert the coordinate values to coordinate values of corresponding pixels on a projection plane at least with respect to voxels having a brightness value higher than a predetermined threshold value, or with respect to a predetermined number of voxels in order from a voxel having a largest brightness value, and to display brightness values of the corresponding voxels for the coordinate values of the pixels obtained by the conversion.

Further features of the present invention will become apparent from the following description of exemplary embodiments with reference to the attached drawings.

BRIEF DESCRIPTION OF THE DRAWINGS

FIG. 8 is a figure showing a data structure example of voxel coordinate data according to Example 1;

DESCRIPTION OF THE EMBODIMENTS

When the observation direction is arbitrarily changed by the user, a very large calculation amount is required in order to specify the row of voxels 2 corresponding to each pixel 4 on the data space 1 and to search for the maximum brightness value. The reason therefor is that even when the voxels 2 belong to the same row in the data space 1, since the voxels are present discontinuously in the data, the number of times of reading and writing data to and from the cache memory having limited storage capacity inevitably increases, and the amount of computation required for retrieving the maximum brightness value corresponding to each voxel row dramatically increases.

Figure 1:
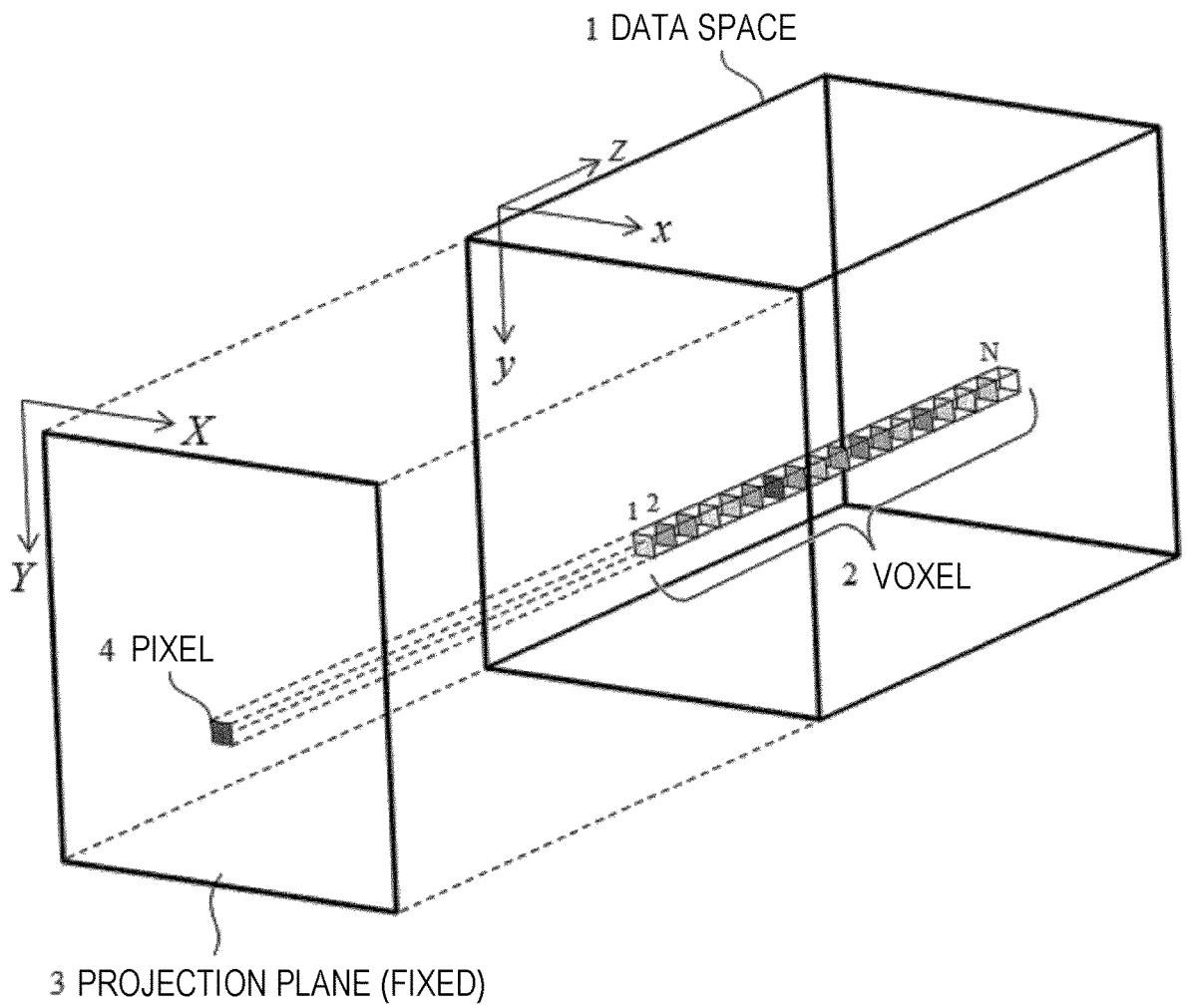
FIG. 1 is a figure illustrating a principle of rendering by a general maximum intensity projection method.
Figure 2:
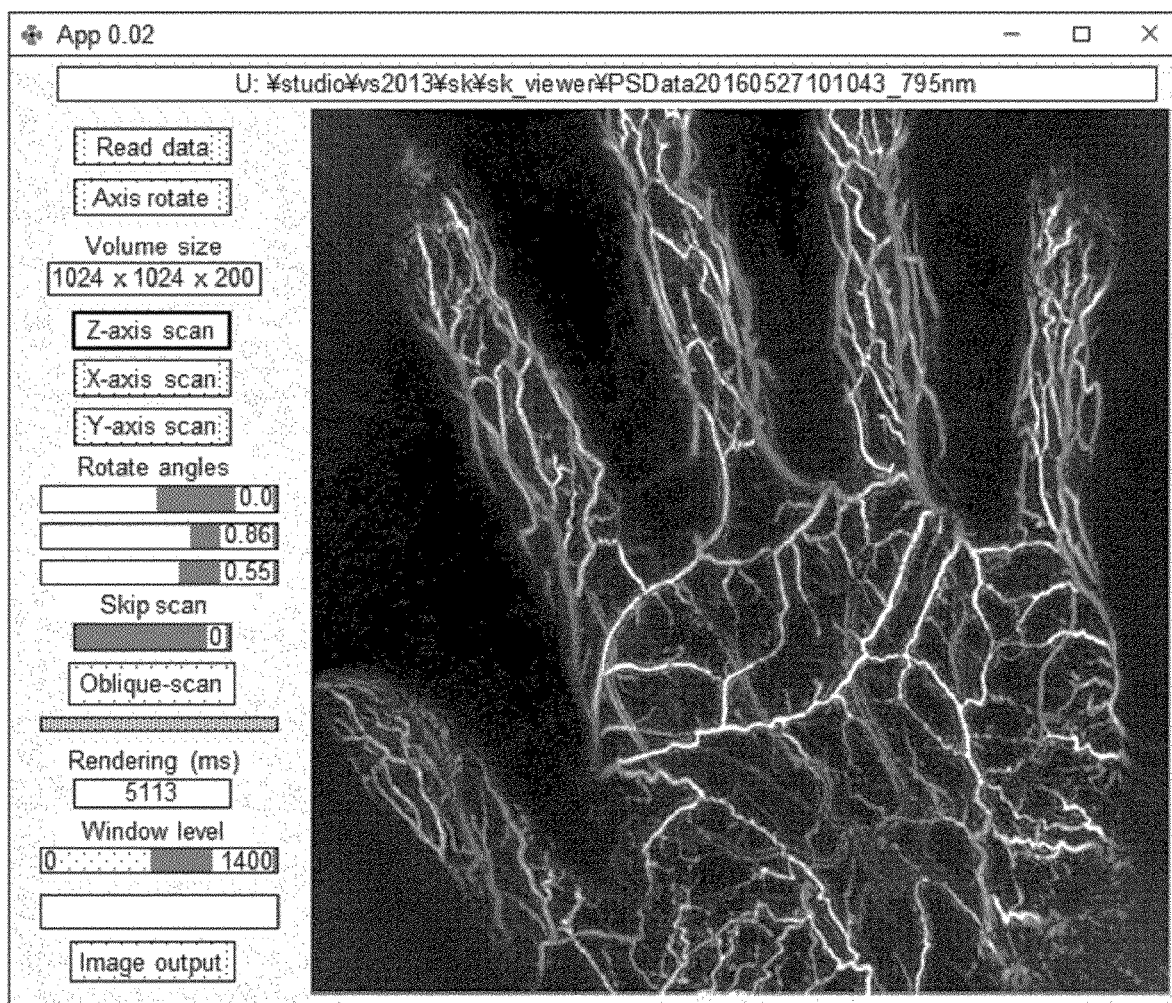
FIG. 2 is a figure showing an example of a maximum intensity projection image obtained by the method illustrated by FIG. 1.
Figure 3:
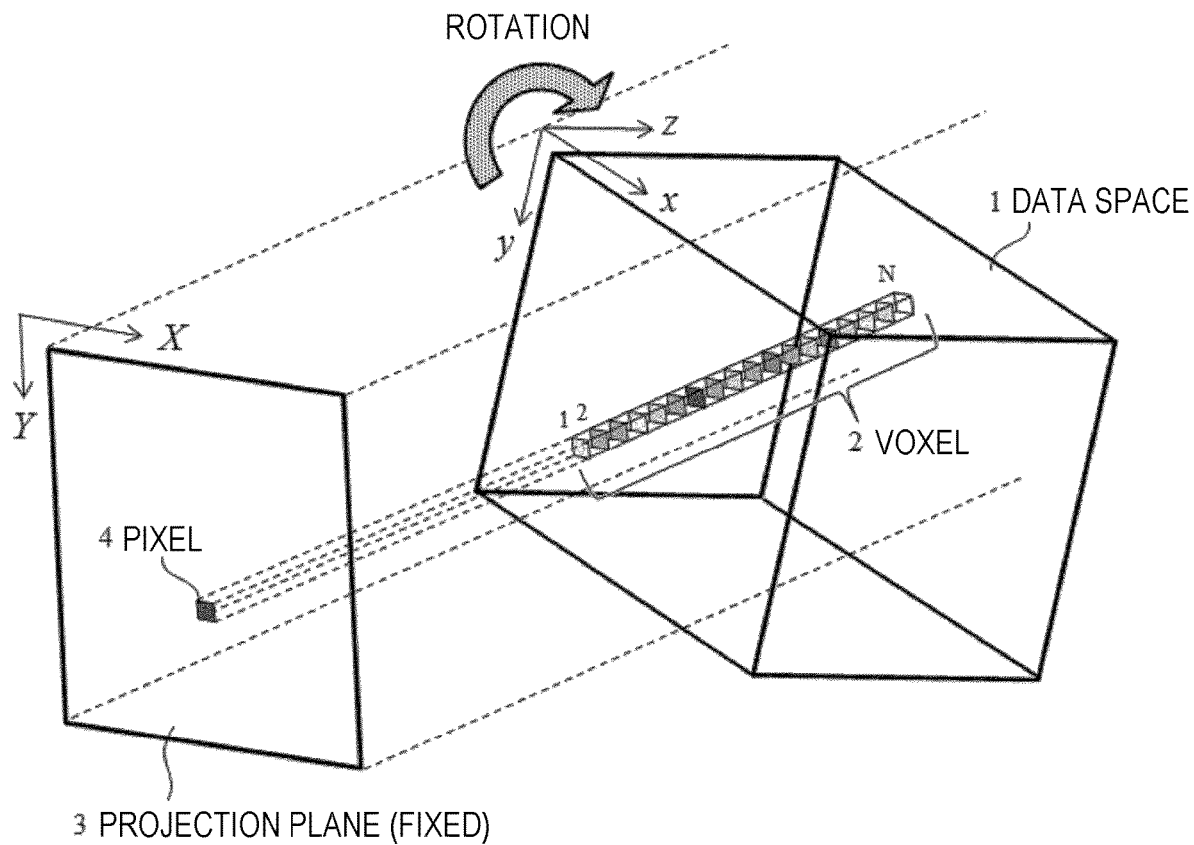
FIG. 3 is a figure illustrating a principle of rendering during rotation display in a general maximum intensity projection method.
Figure 4:
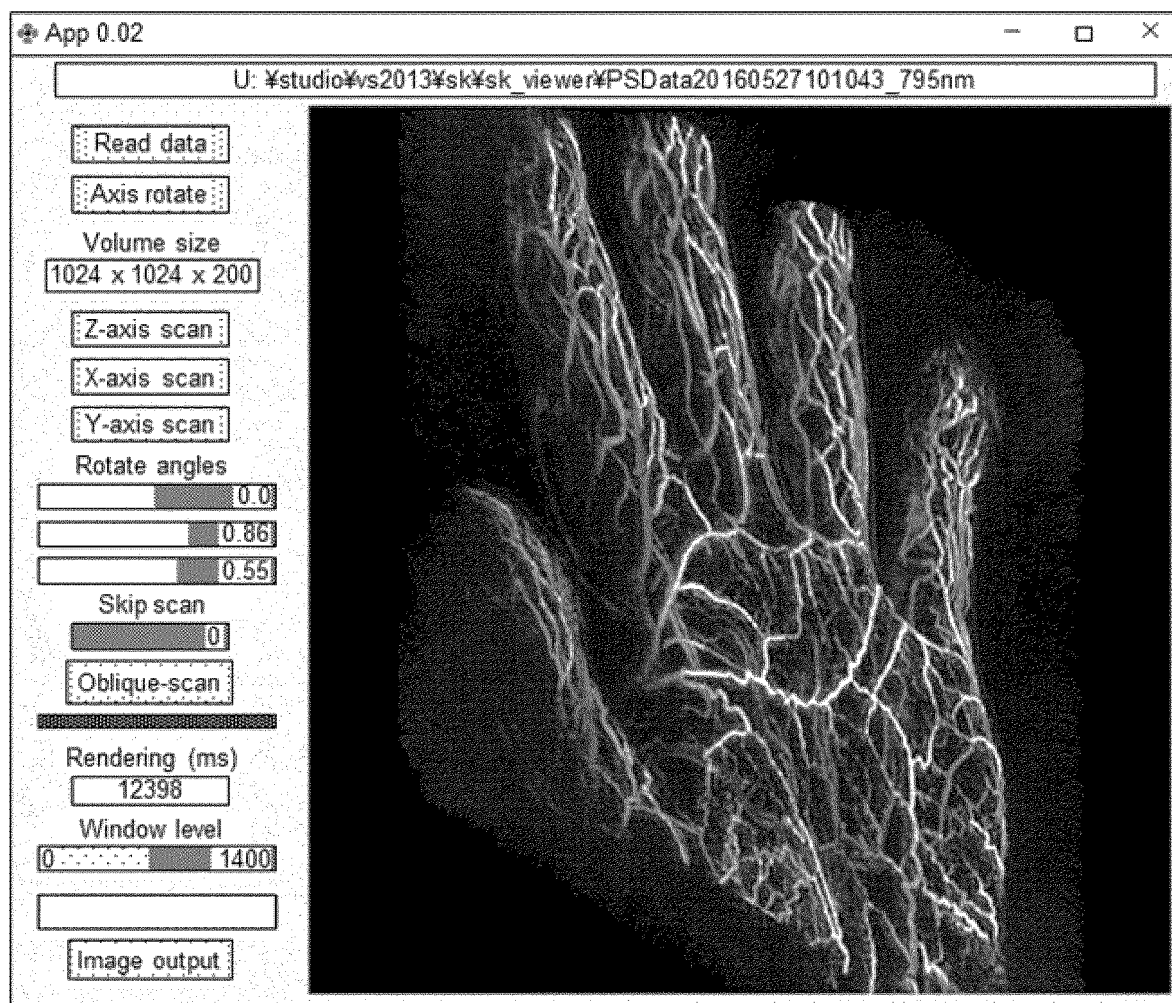
FIG. 4 is a figure showing an example of rotation display of a maximum intensity projection image obtained by the method illustrated by FIG. 3.

In particular, in a notebook PC (Personal Computer), which has a low processing capacity, the rotation, enlargement, reduction, and movement display of images with a large amount of data (for example, several hundred MB) cannot be performed in real time. FIG. 4 illustrates an example of rotation display of the same maximum intensity projection image as shown in FIG. 2. Where the time until the creation of the maximum intensity projection image is measured, 13.2 sec are required when using a single-core CPU. However, a process requiring 13.2 sec to render a maximum intensity projection image after one rotation amount is given is not very usable.

Figure 5:
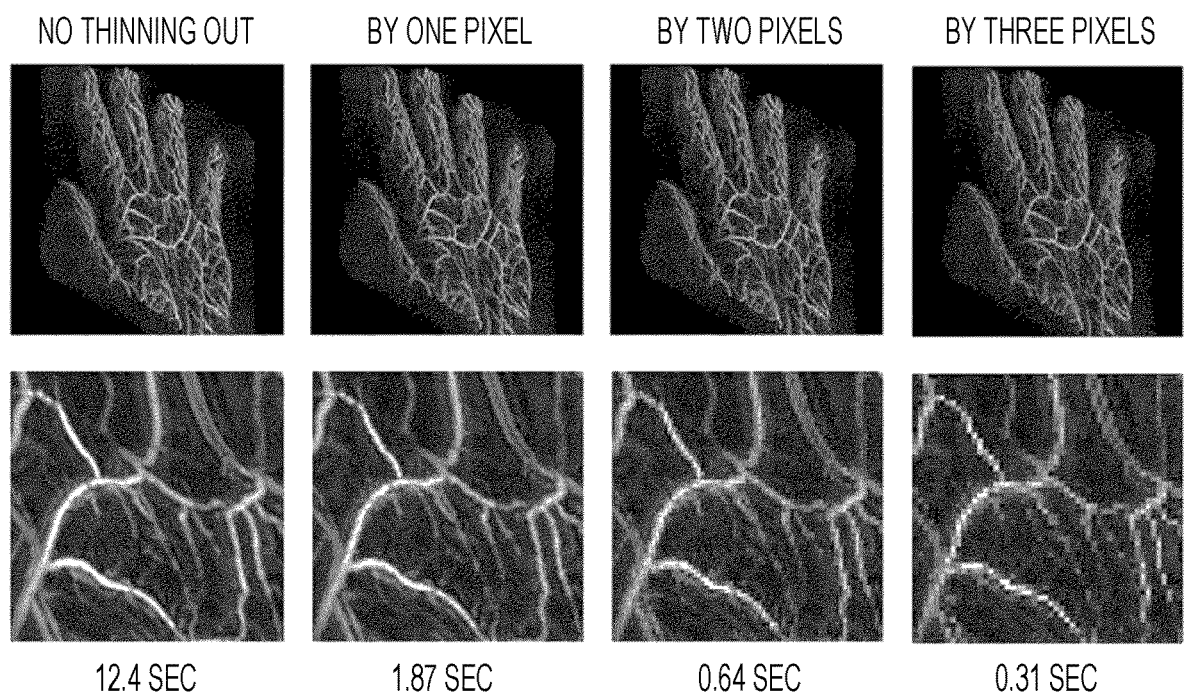
FIG. 5 is a figure explaining a relationship between rendering speed and image quality according to a thinning-out amount.

Also, even in a case of desktop type PCs which have higher processing capability than laptop PCs, when rotation display is performed, computational measures such as thinning-out of data (reduction of resolution and image quality) are used to shorten the calculation time required for rendering. FIG. 5 shows an example of the case where resolution is reduced by combining the thinning-out processing of data. The image at the left end in FIG. 5 corresponds to generating a maximum intensity projection image with no thinning-out, the second image from the left corresponds to generating a maximum intensity projection image by thinning out the pixels by one picture element, the third image from the left corresponds to generating a maximum intensity projection image by thinning out the pixels by two picture elements, and the image at the right end corresponds to generating a maximum intensity projection image by thinning out the pixels by three picture elements.

The upper four diagrams are the whole images of the maximum intensity projection images rendered by using the respective methods, and the lower four images are the images obtained by enlarging a part of each image. As apparent from FIG. 5, it is possible to shorten the processing time by increasing the number of thinned-out picture elements. Meanwhile, as the number of thinned-out picture elements increases, the image quality deteriorates. Thus, in the data thinning-out process, it is difficult to maintain sufficient image quality and perform rotation display of the image.

Accordingly, embodiments of the present invention provides a technique that shortens a processing time required for movement, enlargement, reduction and rotation display of a maximum intensity projection image and, at the same time, ensures good image quality even when using a PC with a low processing capacity.

Embodiments of the present invention will be described below with reference to the drawings. It should be noted that the embodiments of the present invention are not limited to the embodiments described hereinbelow, and various modifications can be made within the scope of the technical idea thereof.

(1) Principle

The inventors focus attention on the sparsity of three-dimensional volume data corresponding to the source data for rendering a maximum intensity projection image, and propose a processing method described hereinbelow. In addition to the above-described photoacoustic imaging data, the three-dimensional volume data in the examples also include three-dimensional image data generated by, for example, an X-ray CT (Computed Tomography) apparatus or an MRI (Magnetic Resonance Imaging) apparatus, and three-dimensional image data generated by a PET (Positron Emission Tomography) apparatus.

Further, the three-dimensional volume data in the examples is not limited to the medical image data, and may be image data obtained on an object or the like other than a human body. The three-dimensional volume data have a greater or lesser sparsity depending on the method for acquiring the source data. The sparsity herein means that data important or meaningful for interpretation are sparsely present within entire data.

Figure 6:
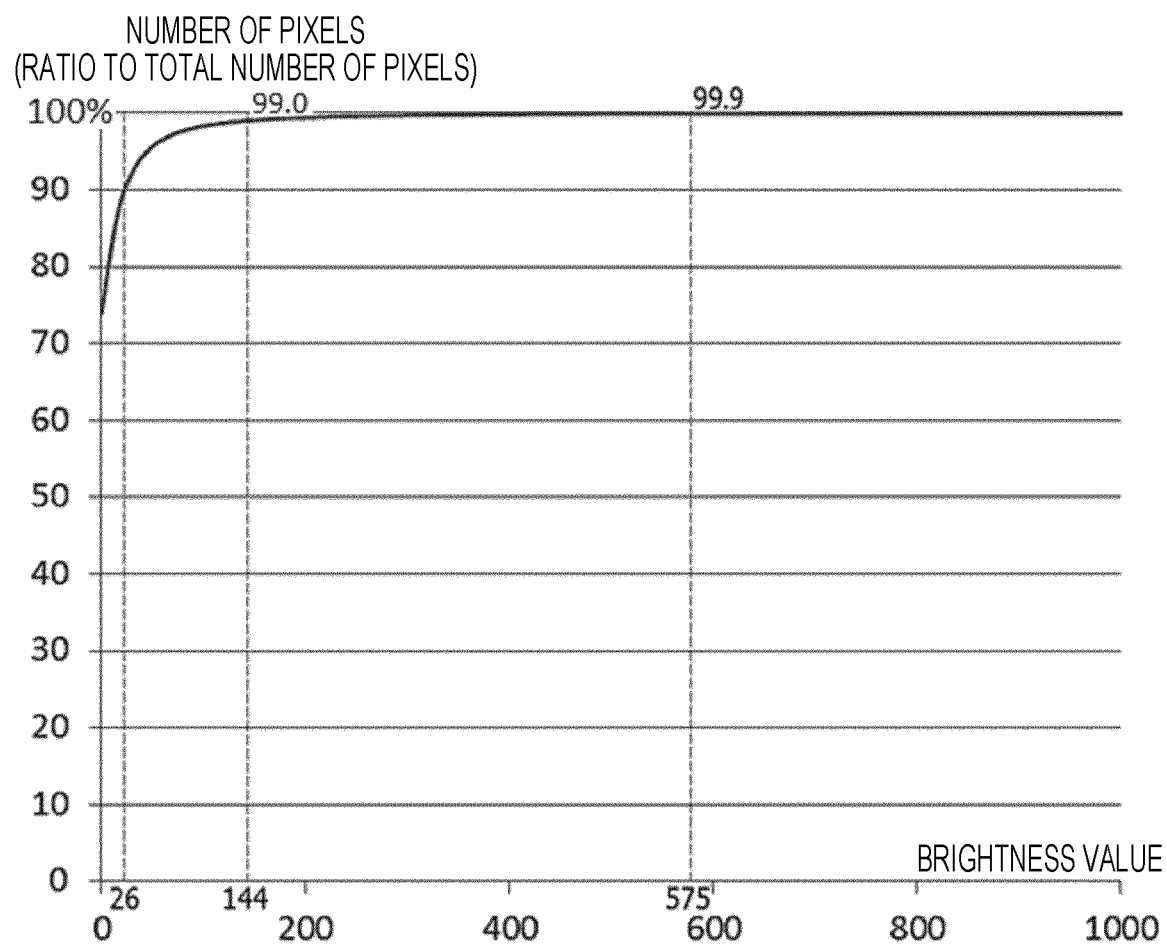
FIG. 6 is a figure illustrating sparsity of photoacoustic imaging data.

For example, the distribution of brightness values in a case of photoacoustic imaging data is shown in FIG. 6. The horizontal axis in FIG. 6 is the brightness value, and the vertical axis is the ratio (percentage) of the number of corresponding picture elements to the total number of picture elements. As described above, a blood vessel to be interpreted is recognized as a high-brightness picture element. However, as shown in the graph of the figure, the brightness value of picture elements included in 90% from the picture element with the smallest brightness value is "26" at the maximum. A picture element with the brightness value of "26" is so dark that it cannot be actually interpreted. That is, 90% of the photoacoustic imaging data are picture elements that do not affect the maximum intensity projection image.

For this reason, the inventors focus attention only on voxels having high brightness value as important or meaningful data for image interpretation, and propose a method of reflecting only the brightness of these voxels on the pixels on the projection plane. In the conventional method, it is necessary to handle all the voxels as objects to be processed in order to specify the voxel row corresponding to the pixel on the projection plane. However, in the method described in the following examples, it is sufficed to use only some of all the voxels constituting the three-dimensional spatial data. Therefore, it is possible to reduce greatly the amount of calculation required for rendering such as coordinate conversion processing. The "maximum intensity projection image", as referred to in the present specification, is assumed to be inclusive of not only a maximum intensity image, but also an image constituted by a brightness value equivalent to the maximum intensity (that is, the brightness value of the voxels having a high brightness value).

In each of the example described below, the brightness value will be discussed as an example, but in place of the brightness value, for example, a color may be used. Therefore, these can be collectively expressed as voxel values.

(2) Example 1

(2-1) Apparatus Configuration

Figure 7:
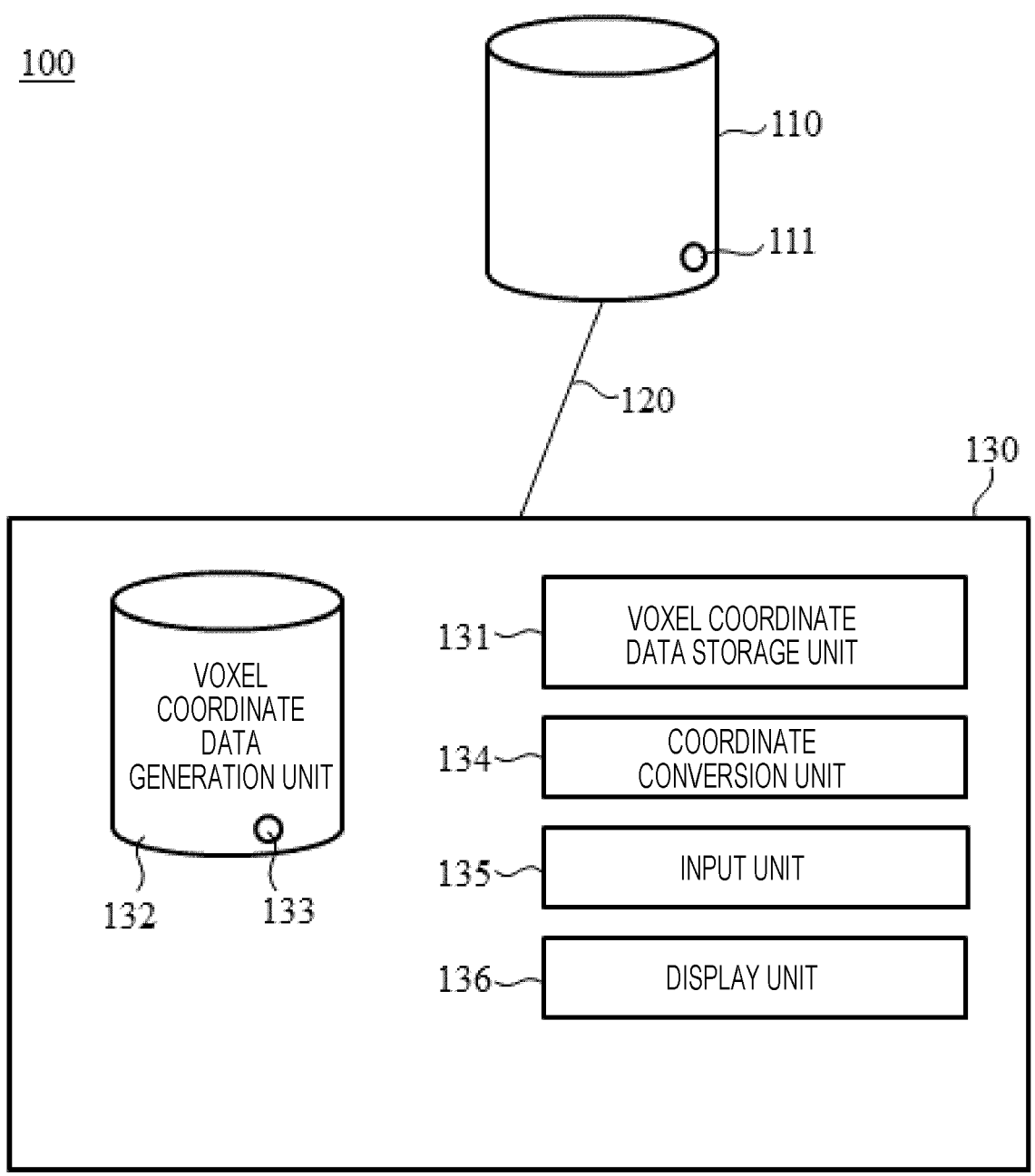
FIG. 7 is a figure showing a configuration example of an image processing apparatus according Example 1.

FIG. 7 shows a configuration example of an image processing system 100 according to the present example. The image processing system 100 includes a server 110 and an image processing apparatus 130. The server 110 and the image processing apparatus 130 are connected through a network 120. The image processing apparatus 130 is used as an input/output apparatus for the server 110. A configuration in which the server 110 and the image processing apparatus 130 are integrated is also possible.

In the server 110, the above-described three-dimensional volume data 111 are stored. The server 110 is configured of a hard disk or other storage device. The three-dimensional volume data 111 are a set of cross-sectional images in which shading is expressed, for example, by a difference in brightness value. In the case of this example, it is assumed that the cross-sectional image is expressed only by the brightness value, but the cross-sectional image may be also expressed using color information (red (R), green (G), and blue (B), or cyan (C), magenta (M), yellow (Y), and black (K)).

The image processing apparatus 130 is configured of a so-called computer. That is, the image processing apparatus 130 is configured of a main storage device, a computing device, a control device, and an input/output device. The image processing apparatus 130 realizes various functions to be described later through execution of corresponding programs. Some or all of the functions may be realized by hardware.

The processing capacity of the CPU constituting the image processing apparatus 130 is not limited, but where the processing capability of the CPU is low, the effect of the processing method according to the examples becomes more prominent. Therefore, in this example, it is assumed that the image processing apparatus 130 is configured of a notebook PC carrying a single-core CPU. Further, it is assumed that the image processing apparatus 130 is equipped with a 64-bit OS of Windows 7 (registered trademark) or a later version.

The image processing apparatus 130 in this example includes a voxel coordinate data generation unit 131, a voxel coordinate data storage unit 132, a coordinate conversion unit 134, an input unit 135, and a display unit 136. It goes without saying that functional units other than those mentioned hereinabove may be installed in the image processing apparatus 130 at the time of mounting. When configuring these functional units as software modules constituting the image processing program, these functional units are stored in a storage device, and the computing device of the image processing apparatus 130 executes these software modules, thereby realizing the functions of the image processing apparatus 130.

Figure 8:
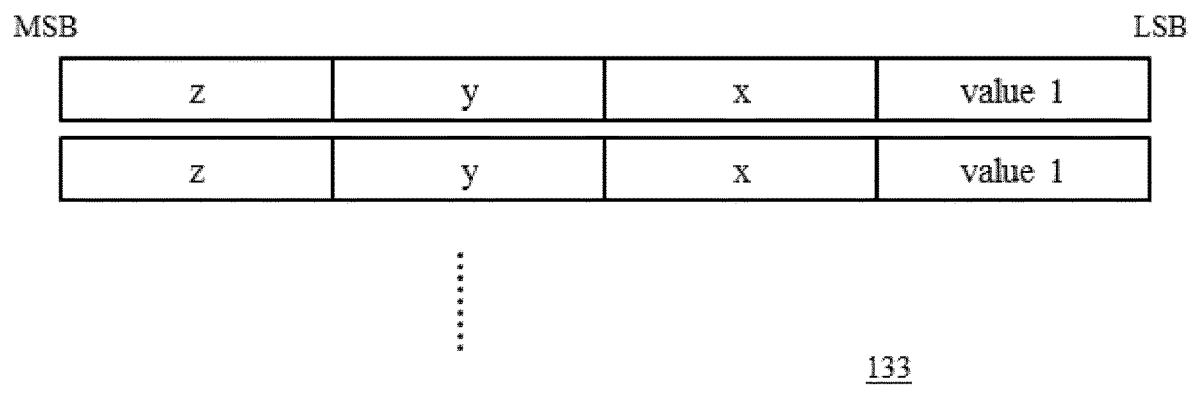

The voxel coordinate data generation unit 131 generates voxel coordinate data 133 by combining corresponding brightness values with the coordinate values of the respective voxels constituting the three-dimensional volume data 111. FIG. 8 shows an example of a data structure of the voxel coordinate data 133 used in this example. In the case of this example, each of the z coordinate, y coordinate, and x coordinate is represented by 16 bits. The brightness value is also represented by 16 bits. That is, one record of the voxel coordinate data 133 corresponding to one voxel is composed of 64 bits (=16 bits×4).

The voxel coordinate data storage unit 132 is a storage area that stores the voxel coordinate data 133. The voxel coordinate data storage unit 132 is configured of a hard disk or other storage device. The voxel coordinate data storage unit 132 stores voxel coordinate data 133 corresponding to all the voxels constituting the three-dimensional space.

The voxel coordinate data generation unit 131 also performs processing of rearranging the voxel coordinate data 133 stored in the voxel coordinate data storage unit 132 in order of magnitude of brightness values. By this rearrangement, the magnitudes of the brightness values to be read to the cache memory can be arranged to substantially the same magnitude. This means that reading and writing of data to and from the cache memory are made more efficient, which contributes to reducing the number of times of reading and writing. Meanwhile, the coordinate values of the voxel coordinate data 133 arranged in the voxel coordinate data storage unit 132 are changed in order of the coordinate values corresponding to the brightness values.

The rearrangement of the voxel coordinate data 133 based on the brightness values does not necessarily need to be the rearrangement in a strict sense. Since the image processing apparatus 130 in the present example uses high brightness values, which are important or meaningful data for image interpretation, in the rendering processing of the maximum intensity projection image, sufficient rendering speed and image quality can be realized even without strict alignment in the brightness value order.

In other words, the rearrangement of the voxel coordinate data 133 may involve the rearrangement in approximate order of magnitude of the brightness values. The rearrangement processing may be performed only once when the voxel coordinate data 133 are generated. Since the amount of calculation required for the rearrangement is small, the processing can be completed in a short time even on a notebook PC. Therefore, the delay in rendering speed due to the rearrangement of the voxel coordinate data 133 practically can be ignored.

When the generation of the voxel coordinate data 133 has already been completed on the server 110 side, the voxel coordinate data generation unit 131 may execute only the rearrangement processing of voxel coordinate data 133 which are to be read.

Figure 9:
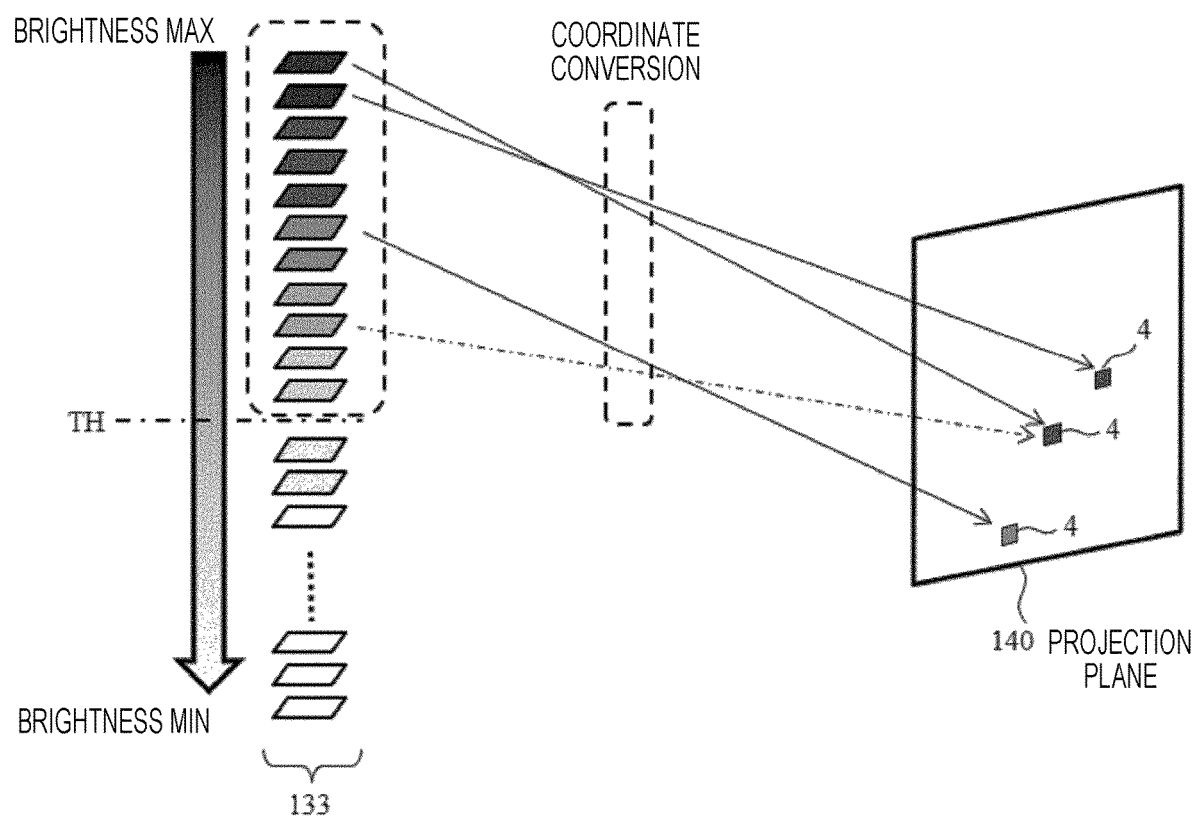
FIG. 9 is a figure illustrating an image of a coordinate conversion operation according to Example 1.

Next, an image of coordinate conversion is shown in FIG. 9. The coordinate conversion unit 134 executes the processing of reading the rearranged voxel coordinate data 133 by a predetermined number thereof to the cache memory and converting the corresponding coordinate values to the coordinate values of pixels on the projection plane 140. As shown in FIG. 9, in the case of this example, the direction of the coordinate conversion is from the coordinate values of the voxel to the coordinate values of the pixel, which is opposite to that in the conventional method. That is, in the case of the present example, the coordinate (dependent variable) is represented by the function of brightness (independent variable), which is different from the conventional method in which the brightness (dependent variable) is represented by a function of coordinate (independent variable). Therefore, it is also possible to convert the coordinate values of a plurality of voxel coordinate data 133 to the coordinate values of one pixel 4.

The coordinate conversion unit 134 executes processing of allocating the brightness values of the voxel coordinate data 133 serving as a conversion source to the coordinate values of the pixels obtained by the conversion. Where another brightness value has already been allocated to the same pixel, the coordinate conversion unit 134 gives higher priority to the higher brightness value. This is for rendering the maximum intensity projection image. When the above-described rearrangement processing is executed in a strict sense, the brightness value to be allocated later will not become larger than the already allocated brightness value. Therefore, when the rearrangement processing is strictly executed, the process of determining the magnitude relation with the already allocated brightness value can be omitted.

Further, when a change of the observation direction (the rotation of the projection plane 140 or the rotation of the three-dimensional volume data 111) is inputted through the input unit 135 in the course of rendering the maximum brightness value on the projection plane 140, the coordinate conversion unit 134 cancels the present rendering and executes coordinate conversion and rendering processing corresponding to the newly designated observation direction. Since the rendering of the maximum intensity projection image is completed in a short time, as will be described later, the contents of the maximum intensity projection image which is rendered following the operation of the user can be substantially (or physically) continuously updated.

In the present example, the coordinate conversion unit 134 executes the aforementioned coordinate conversion processing in two stages. In the processing of the first stage, the aforementioned coordinate conversion and allocation of brightness value are executed with respect to voxels having a brightness value higher than a predetermined threshold value given in advance, or with respect to up to a predetermined number of voxels in order from a voxel having a largest brightness value.

The threshold value of the brightness value and the threshold value of the number of voxels depend on the distribution of brightness values in the three-dimensional volume data 111 to be used for rendering the maximum intensity projection image. In the case of the present example, the threshold values set to about several percent, for example, to 10%, from the side with a high brightness value. This is because in the case of the maximum intensity projection image, as described above, even when a low-brightness value is used for rendering, the observed image itself hardly changes. It is desirable that the threshold value could be freely changed by the user.

In the processing of the second stage, the coordinate conversion processing is executed with respect to the remaining voxel coordinate data 133 which have not been the target of processing of the first stage. By converting the coordinate values of all the remaining voxel coordinate data 133 to the coordinate values of the pixels 4 on the projection plane 140 and allocating the corresponding brightness values, it is theoretically possible to enhance the renderability of details of the maximum intensity projection image. Since the brightness value becomes smaller and smaller, a brightness value is not allocated to the pixels to which a brightness value has already been allocated.

The coordinate conversion unit 134 is also equipped with a function of rendering an enlarged image or a reduced image. In the case of enlarging a maximum intensity projection image rendered on the projection plane 140, the coordinate conversion unit 134 linearly interpolates, according to an enlargement ratio, a partial region of the maximum intensity projection image rendered on the projection plane 140 to generate an enlarged image. Meanwhile, when reducing the maximum intensity projection image rendered on the projection plane 140, the coordinate conversion unit 134 uses the brightness value of the voxel coordinate data 133 for the pixel on the projection plane 140 reduced in accordance according to a reduction ratio, thereby generating a reduced image. In either case, since the calculation load is small, it is possible to change the rendering contents within a short time.

The input unit 135 is used for inputting an observation direction, a threshold value, and the like. The observation direction can be inputted by a method of inputting the rotation direction of the three-dimensional volume data 111 with respect to the projection plane 140 which is a fixed surface, and a method of inputting the rotation direction of the projection plane 140 to the fixed three-dimensional volume data 111. Which method to use may be selected by the user. The display unit 136 is configured of a liquid crystal display or other display device. An interface screen such as shown in FIGS. 2 and 4 is displayed on the display unit 136. Here, the display unit 136 does not need to be integrated with the image processing apparatus 130, and may be externally attached to the image processing apparatus 130.

(2-2) Rendering Processing Operation

Figure 10:
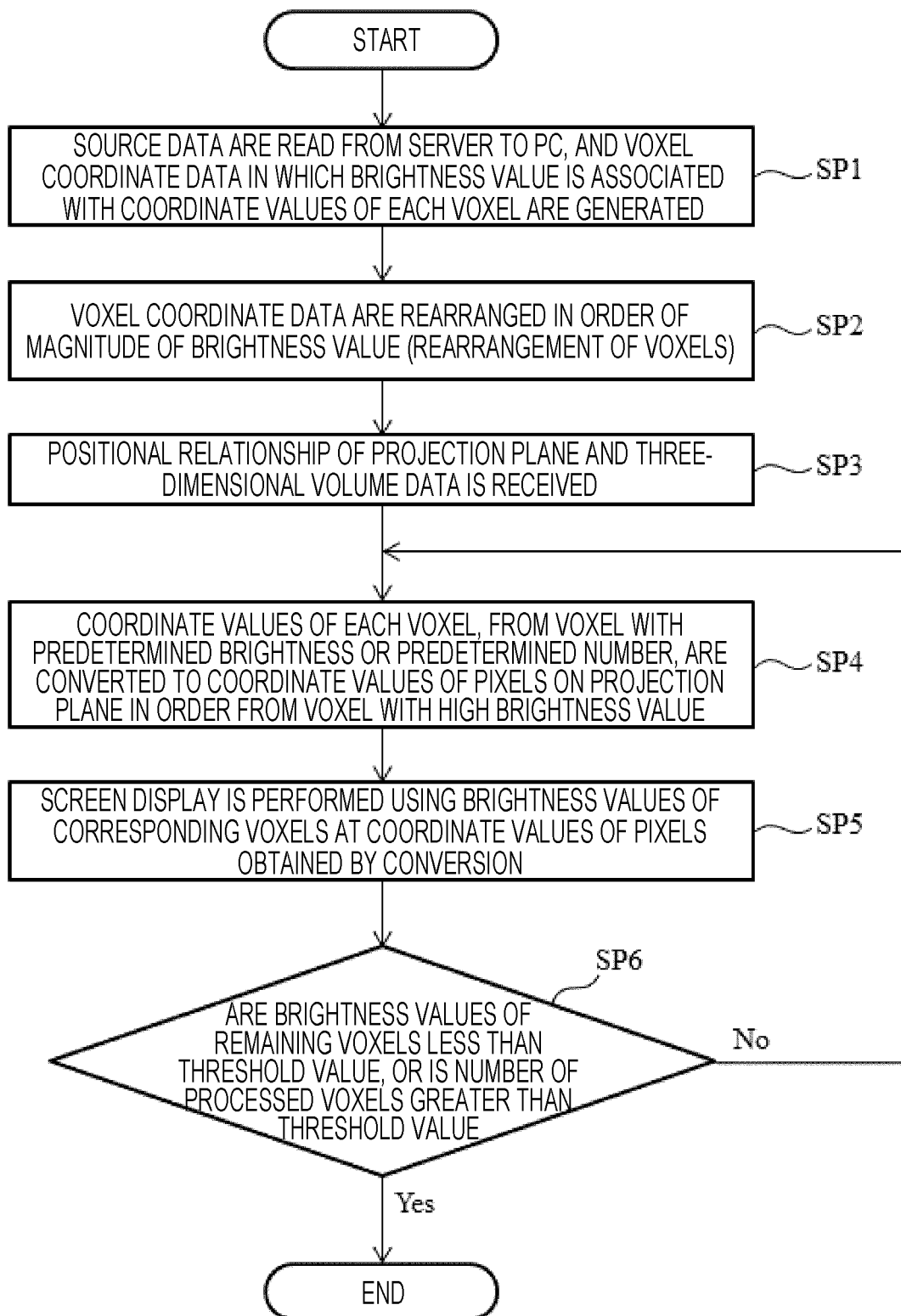
FIG. 10 is a flowchart for explaining the rendering processing operation according to Example 1.

The rendering processing operation according to the present example will be described hereinbelow with reference to FIG. 10. The processing operation is realized through execution of a program by the image processing apparatus 130. First, the voxel coordinate data generation unit 131 reads the three-dimensional volume data 111 from the server 110 and generates the voxel coordinate data 133 having a data structure shown in FIG. 8 (step SP1). Subsequently, the voxel coordinate data generation unit 131 rearranges the voxel coordinate data 133 in order of magnitude of the brightness value (step SP2).

Thereafter, the coordinate conversion unit 134 receives the positional relationship between the projection plane 140 inputted through the input unit 135 and the three-dimensional volume data 111 and determines a conversion formula for converting the coordinate values of the voxels on the three-dimensional volume data 111 to the coordinate values of the pixels on the projection plane 140 (step SP3).

Thereafter, the coordinate conversion unit 134 reads the rearranged voxel coordinate data 133 by a predetermined number thereof to the cache memory in order from the largest brightness value and converts the corresponding coordinate values to the coordinate values of the pixels on the projection plane (step SP4). Further, the coordinate conversion unit 134 uses the brightness value corresponding to the converted coordinate values to display a screen (step SP5). At this time, for the same pixel, the coordinate conversion unit 134 gives priority to a larger brightness value at all times.

Thereafter, the coordinate conversion unit 134 determines whether the brightness value of the remaining voxel is smaller than the threshold value or whether the number of processed voxels is larger than the threshold value. Where a negative result is obtained, the coordinate conversion unit returns to step SP4 and repeats the rendering (step SP6). Meanwhile, where a positive result is obtained in step SP6, the coordinate conversion unit 134 finishes the rendering processing of the maximum intensity projection image. Finishing the rendering processing here means finishing the rendering processing of the abovementioned first stage, and when the user does not input a viewing direction change or the like, the rendering process of the second stage is started.

(2-3) Effect

Figure 11:
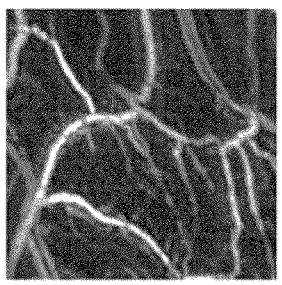
FIG. 11 is a figure illustrating the relationship between the time required for rendering the maximum brightness value image and the image quality in the rendering processing method according to Example 1.
Figure 11:
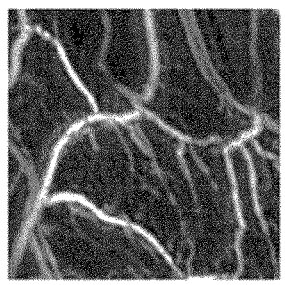
Figure 11:
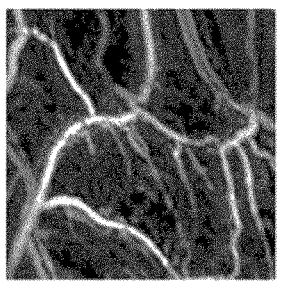
Figure 11:
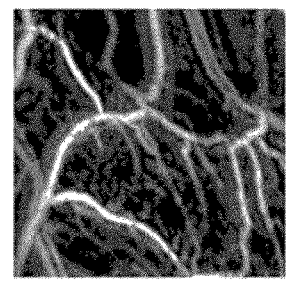
Figure 11:
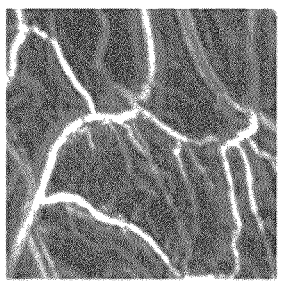
Figure 11:
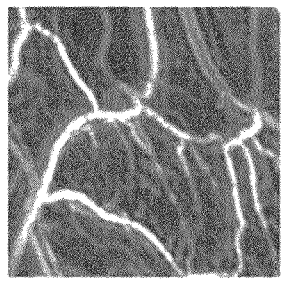
Figure 11:
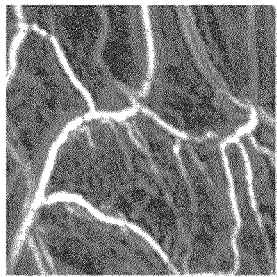
Figure 11:
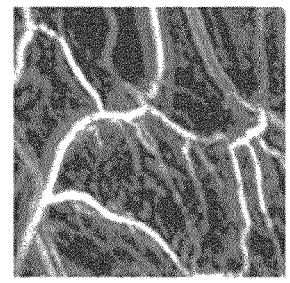

By using the image processing system 100 according to the present example as described above, it is possible to display the maximum intensity projection image of high image quality in a shorter period of time as compared with the conventional method. FIG. 11 shows the relationship between the time required for rendering the maximum intensity projection image and the image quality according to the present example. FIG. 11 shows the case where the three-dimensional volume data 111 are composed of 1024×1024×200 voxels and the projection plane 140 is composed of 1024×1024 pixels as in the case illustrated by FIGS. 2 and 4 hereinabove.

From FIG. 11 it is understood that 0.56 sec is required for rendering the maximum intensity projection image when upper 10% from the voxel with the largest brightness value among the total number of voxels is used. Similarly, 0.31 sec is required for rendering the maximum intensity projection image when upper 5% is used, 0.18 sec is required for rendering the maximum intensity projection image when upper 2.5% is used, and 0.12 sec is required for rendering the maximum intensity projection image when upper 1.25% is used. Each number of seconds is less than that required for the thinning-out processing explained with reference to FIG. 5. The upper row of FIG. 11 shows, for comparison with FIG. 5, the results of calculation performed using a single-core CPU.

Further, the images in the lower row of FIG. 11 are displayed by adding 50 to the brightness level of the images in the upper row in order to emphasize deterioration of image quality, but no difference in image quality can be recognized between the four examples shown in FIG. 11. This is a major difference from the conventional method shown in FIG. 5 in which the image quality deteriorates as the thinning-out number increased. That is, according to the method of this example, it is possible not only to render the maximum intensity projection image in a short time but also to realize rendering with high image quality. Moreover, even when the number of voxels used for rendering is reduced, the image quality of the maximum intensity projection image to be rendered hardly decreases, so even when the number of voxels to be handled increases, the time required for rendering can be set within a range that does not hinder practical use.

Further, in the image processing system 100 according to the present example, since only the voxel coordinate data 133 having a small data size, as compared with the three-dimensional volume data 111, may be stored on the image processing apparatus 130 side, it is possible to avoid a decrease in the operation speed of the image processing apparatus 130 having limited hardware resources.

(3) Example 2

(3-1) Apparatus Configuration

The basic configuration of the image processing system 100 according to the present example is the same as that of Example 1. The difference is in the data structure of the voxel coordinate data 133. In Example 1 described above, the case has been described in which a data structure (FIG. 8) is used in which brightness values corresponding to the coordinate values of the respective voxels in the data space constituted by the three-dimensional volume data 111 are combined.

Figure 12:
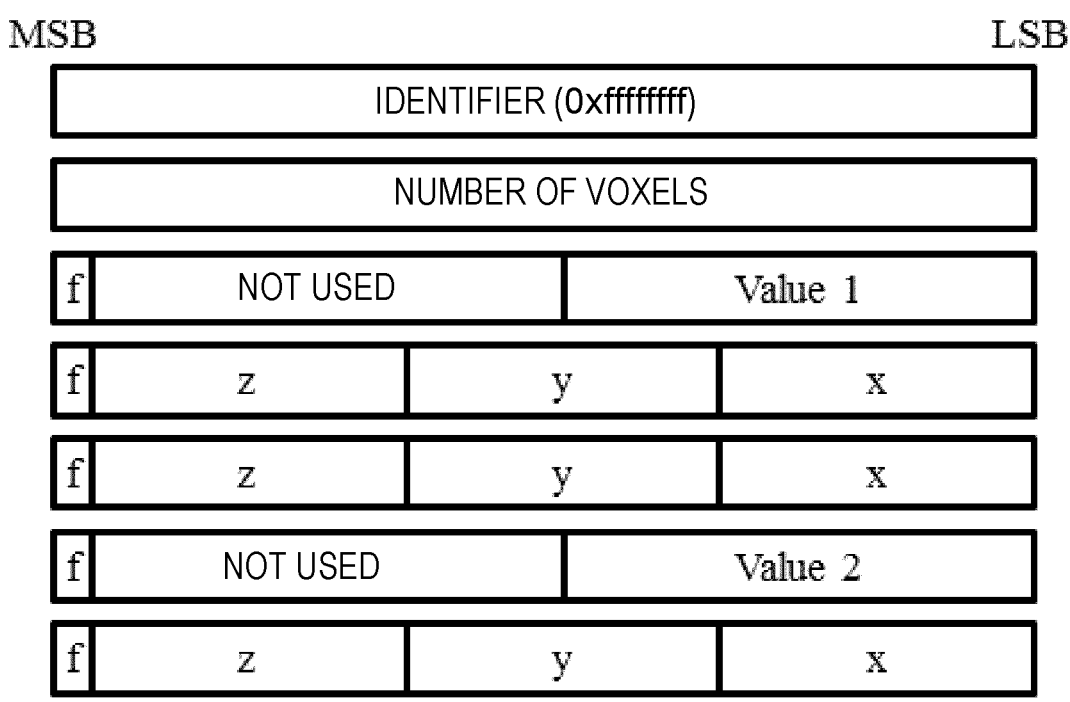
FIG. 12 is a figure showing a data structure example of voxel coordinate data according to Example 2.

Meanwhile, in this example, the voxel coordinate data 133 of the data structure shown in FIG. 12 are used. As can be seen from FIG. 12, in this example, a method of integrating coordinate values of voxels by brightness value units is used. That is, one or a plurality of coordinate values is stored in association with one brightness value (value 1, value 2, . . . ).

In FIG. 12, one record is 32 bits, and 10 bits are allocated to each of the z coordinate, y coordinate, and x coordinate. A 2-bit flag f is allocated to each record. The flag f is used to identify whether each record is a density value or a coordinate value.

In the case illustrated by FIG. 12, the number of voxels is stored in the second record (the second record from the top). In the upper record, a brightness value higher than the brightness value placed in the lower record is arranged. Therefore, by sequentially processing from the upper record, it is possible to eliminate the necessity of comparing the magnitude relation between the brightness value already allocated to the pixel and the brightness value to be newly allocated.

Further, in the case of the data structure shown in FIG. 12, the number of bits constituting one record is only half that of the data structure (FIG. 8) of Example 1. Therefore, the data structure used in this example is suitable for use in the image processing apparatus 130 having a low storage capacity.

(3-2) Rendering Processing Operation

Figure 13:
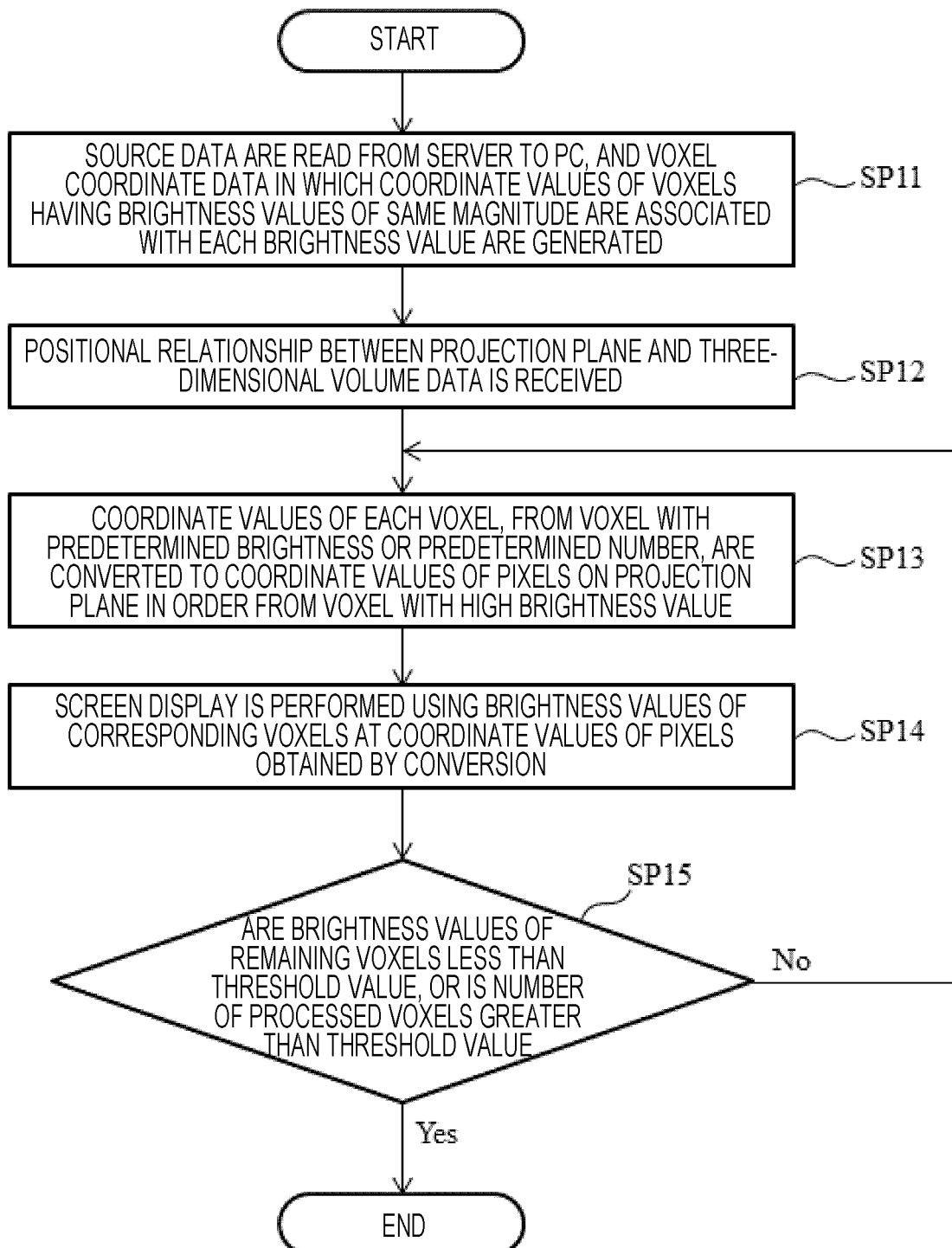
FIG. 13 is a flowchart for explaining the rendering processing operation according to Example 2.

FIG. 13 illustrates the rendering processing operation according to the present example. The processing operation is also realized through execution of a program by the image processing apparatus 130. First, the voxel coordinate data generation unit 131 reads the three-dimensional volume data 111 from the server 110 and generates voxel coordinate data 133 of the data structure shown in FIG. 12 (step SP11). In the case of the present example, once time when the voxel coordinate data 133 have been generated, rearrangement in order of the magnitude of the coordinates is completed.

Next, the coordinate conversion unit 134 receives the positional relationship between the projection plane 140 inputted through the input unit 135 and the three-dimensional volume data 111 and determines a conversion formula for converting the coordinate values of the voxels on the three-dimensional volume data 111 to the coordinate values of the pixels on the projection plane 140 (step SP12).

Subsequently, the coordinate conversion unit 134 reads the coordinate values of the voxels corresponding to order of magnitude of brightness values to the cache memory and converts these coordinate values to the coordinate values of the pixels on the projection plane 140 (step SP13). Further, the coordinate conversion unit 134 uses the brightness values corresponding to the converted coordinate values to display a screen (step SP14). In the case of this example, since the brightness value to be allocated later is always smaller, the coordinate conversion unit 134 does not perform comparison processing even when brightness values allocated to the same pixel are generated.

Thereafter, the coordinate conversion unit 134 determines whether the brightness value of the remaining voxel is smaller than the threshold value or whether the number of processed voxels is larger than the threshold value. Where a negative result is obtained, the coordinate conversion unit 134 returns to step SP13 and repeats the rendering (step SP15). Meanwhile, where a positive result is obtained in step SP15, the coordinate conversion unit 134 finishes the rendering processing of the maximum intensity projection image. Finishing the rendering processing here means finishing the rendering processing of the abovementioned first stage, and when the user does not input a change of viewing direction or the like, the rendering process of the second stage is started.

(3-3) Effect

By using the image processing system 100 according to the present example as described above, the same effect as that of Example 1 can be obtained. That is, it is possible to create a maximum intensity projection image of high image quality in a short time as compared with the conventional maximum intensity projection method. In addition, in the case of this example, since the data size of the voxel coordinate data 133 is only half that of Example 1, these data are suitable for loading in the image processing apparatus 130 having a low storage capacity.

(4) Example 3

(4-1) Apparatus Configuration

The basic configuration of the image processing system 100 according to the present example is the same as that of Example 1. The difference from Example 1 is mainly in the rendering processing operation for displaying the voxel coordinate data 133 on the display unit 136.

The data structure of Example 1 and Example 2 or other data structure may be used as the data structure of the voxel coordinate data 133 according to the present example.

(4-2) Rendering Processing Operation

The rendering processing operation according to the present example will be described hereinbelow. In Example 1 and Example 2, conversion to coordinate values of pixels on the projection plane was performed with respect to voxels having a brightness value higher than the preset threshold value of brightness values, or with respect to up to a predetermined number of voxels in order from a voxel having a largest brightness value. However, depending on the projection direction, it is possible that the voxels be associated only with a very small number of pixels constituting the projection plane and that most of the pixels constituting the projection plane do not have the associated voxels. Assuming that the brightness value of a pixel having no associated voxel is displayed as, for example, zero, when the user changes the projection direction, since the number of pixels with the brightness value of zero changes depending on the projection direction, the user may feel discomfort. Therefore, in this example, a threshold values set for the number of pixels on the projection plane that are associated with voxels.

As an example, when a threshold values set at 70% or more of the number of pixels constituting the projection plane, the coordinate values are sequentially converted to the coordinate values of the pixels on the projection plane, starting from the voxel with the largest brightness value until the voxels are associated with at least 70% of the total number of pixels. As a result, even when the user arbitrarily changes the observation direction, brightness values other than zero are allocated to the same number of pixels, so that the user can perform the observation without feeling discomfort.

Further, similarly to Example 1 and Example 2, a configuration may be used in which a threshold value is set for the brightness value and a threshold value is also set for the number of pixels on the projection plane which are to be associated with the voxels.

As an example, it is assumed that a threshold value is set for the brightness value so that conversion to the coordinate values of pixels on the projection plane is performed with respect to the voxels having a brightness value of the top 5% among the voxels constituting the three-dimensional volume data. It is also assumed that a threshold value is set for the number of pixels so that voxels are associated with 50% or more of the pixels constituting the projection plane. At this time, where the coordinates of the voxels are converted to the coordinates on the first projection plane, even when the voxels having the brightness value of the top 5% are projected onto the first projection plane, a case can occur in which voxels are associated only with less than 50% of the pixels constituting the first projection plane. In such a case, the image processing apparatus 130 gives priority to the threshold value relating to the number of pixels rather than the threshold value of the brightness value, so that coordinate conversion to the first projection plane may be performed with respect to the number of voxels larger than that of the voxels having the brightness value of the top 5%. The image processing apparatus 130 may determine whether or not the condition relating to the number of pixels is satisfied every time the coordinate conversion is performed on one voxel below the threshold value of the brightness value, or may determine whether or not the condition relating to the number of pixels is satisfied each time coordinate conversion is performed on the predetermined number of voxels, for example, 1% of the voxels.

The threshold value related to the brightness value and the threshold value related to the number of pixels may be inputted by the user via the input unit 135. This is the same as in Examples 1 and 2.

(4-3) Effect

As described above, according to the present example, it is possible to provide a display which is unlikely to make the user to feel discomfort regardless of the observation direction while obtaining the same effect as in Example 1.

(5) Example 4

Another example according to the present invention will be described hereinbelow.

In the foregoing examples, the processing of converting the coordinate values of voxels to the coordinate values of corresponding pixels on the projection plane is performed with respect to voxels having a brightness value higher than a predetermined threshold value, or with respect to up to a predetermined number of voxels in order from a voxel having a largest brightness value. By setting the predetermined threshold value or the predetermined number of voxels in consideration of the storage capacity of the cache memory, it is possible to shorten the processing time of the maximum intensity projection image.

As described above, the cache memory has limited storage capacity. Therefore, by determining a predetermined threshold value with respect to the brightness value or a predetermined number of voxels so that the amount of data to be used for the conversion of the coordinate values falls within the capacity of the cache memory, it is possible to reduce the number of data write/read operations to/from the cache memory.

As an example, the image processing apparatus 130 determines a threshold value or the number of voxels corresponding to the capacity of the cache memory, and performs coordinate conversion onto the projection plane with respect to the voxels determined according to the determined threshold value or number of voxels.

When the user inputs a threshold value or number of voxels via the input unit 135, the image processing apparatus 130 may compare the inputted threshold value or number of voxels with that previously stored in the storage device and corresponding to the capacity of the cache memory. The image processing apparatus 130 may notify the user of the comparison result. For example, when the amount of data of voxels determined by the value inputted by the user is larger than the amount of data of voxels determined by the value which has been stored in advance, the user can realize high-speed processing by changing the threshold value or the number of voxels so that the amount of data of voxels to be used for data conversion falls within the capacity of the cache memory. Meanwhile, when the amount of data of voxels determined by the value inputted by the user is larger than the amount of data of voxels determined by the value which has been stored in advance, the user can observe an image with a higher resolution, without greatly reducing the speed of rendering processing, by changing the threshold value or the number of voxels.

The image processing apparatus 130 may be configured to use a threshold value or number of voxels corresponding to the capacity of the cache memory as a default value.

According to the present example, by reducing the frequency of writing and reading data to and from the cache memory, it is possible to shorten the time required for rendering the projection image.

(6) Example 5

Still another example according to the present invention will be described hereinbelow.

In the present example, the image processing apparatus 130 sets at least one of a predetermined threshold value and a predetermined number of voxels according to the processing capability of the image processing apparatus 130.

Where the threshold value or the number of voxels inputted by the user via the input unit 135 is followed, excessive time may be required for rendering the projection image due to limited processing capability of the image processing apparatus 130. Therefore, in the present example, at least one of the threshold values and the predetermined number of voxels is set so that when the user performs input to change the observation direction in order to view an image from a plurality of observation directions, the projection image after the change of the observation direction is displayed on the display unit within a predetermined time. The predetermined time is, for example, the refresh rate of the display device. After receiving the input for changing the observation direction, the image processing apparatus 130 can display the image after the observation direction change within a predetermined frame.

The image processing apparatus 130 according to the present example includes a processing capability acquisition means for acquiring processing capability information related to image display, for example, an operation frequency of the CPU constituting the image processing apparatus 130, the number of cores, a cache memory capacity, a capacity of the storage device, an access speed, a refresh rate of the display unit 16, and the like. The processing capability acquisition means may be realized in a form in which the main storage device stores the abovementioned processing capability information in advance or may be realized as some of the functions of the installed OS.

The image processing apparatus 130 may compare the threshold value or the number of voxels inputted by the user with a threshold value or number corresponding to the processing capability information. The image processing apparatus 130 may notify the user of the comparison result. The user can change the threshold value or the number of voxels according to the notified comparison result.

Further, when all the voxels which are determined according to the threshold value or the number of voxels inputted by the user and which are to be used for the coordinate conversion cannot be displayed within the above-mentioned predetermined period of time, the voxels that can be displayed within the predetermined time are displayed first and the voxels that cannot be displayed within the predetermined period of time may be displayed later.

Figure 14:
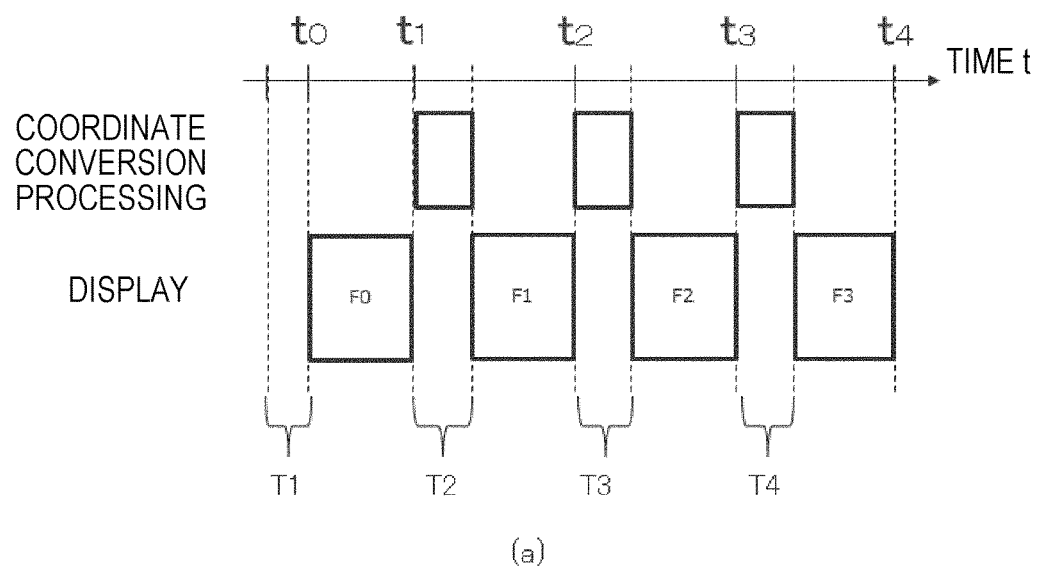
FIG. 14 is a figure illustrating the rendering processing operation according to Example 5.
Figure 14:
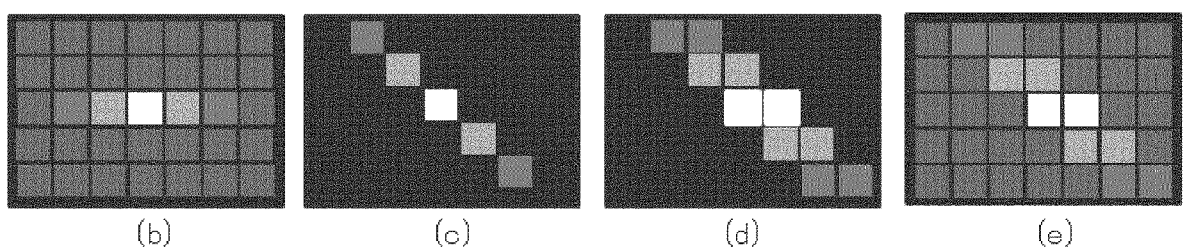

FIG. 14 shows an example of coordinate conversion and display processing. In FIG. 14, (a) shows time series of coordinate conversion processing for converting coordinate values of voxels to coordinate values of pixels on the projection plane and display processing of projection image.

In a period T1, there is no instruction to change the observation direction, enlarge, or reduce, so at a time t0, an image corresponding to a previous instruction is displayed. In FIG. 14, (b) shows an example of the image displayed at time t1.

Where the user gives an instruction to change the observation direction at the time t1, the image processing apparatus 130 executes the coordinate conversion processing, performs the coordinate conversion processing on the number of voxels that can be processed within a period T2, and performs the display processing at the timing subsequent to the period T2. An image displayed at a time t2 is shown in (c) of FIG. 14. Here, since the number of voxels that can be subjected to coordinate conversion within the period T2 is limited, pixels having no associated voxel are displayed in black.

Next, it is assumed that an enlargement instruction is issued from the user at the time t2. In accordance with the enlargement instruction, the image processing apparatus 130 executes coordinate conversion processing of voxels to the projection plane after the enlargement, and performs the display processing at the timing subsequent to a period T3. An image displayed at a time t3 is shown in (d) of FIG. 14. Here, since the number of voxels that can be processed within the period T3 is limited, pixels having no associated voxel are displayed in black.

At the time t3, since there is no instruction from the user, the coordinate conversion processing is executed within a period T4 with respect to the voxels for which the coordinate conversion processing has not been completed within the period T3. Then, the display processing is performed at the timing subsequent to the period T4. An image displayed at a time t4 is shown in (e) of FIG. 14. In (d) of FIG. 14, the voxel association mode can be also understood for the pixels colored black.

By performing the operations described with reference to (a) to (e) of FIG. 14, the image processing apparatus 130 can display, after the user stopped issuing the instructions, the voxels that cannot be processed within a predetermined time (here, within the image display interval) by quickly following the instruction from the user.

The image processing apparatus 130 may be configured to use at least one of the threshold value and the number of voxels corresponding to the processing capability information as a default value.

According to the present example, when an input to change the observation direction is made, it is possible to set at least one of the threshold value and the predetermined number of voxels on the basis of the processing capability information, so as to display the projection image after the change in the observation direction on the display unit within a predetermined time. As a result, it is possible to reduce the extension of time until the image after the change in the observation direction is displayed.

This example is particularly useful when the image processing apparatus 130 is configured using a device having low processing capability such as a notebook PC, a tablet PC, a smartphone, or the like. For example, by displaying the image after the change in the observation direction within a predetermined frame, the user can change the observation direction variously without feeling stress.

(7) Example 6

Still another example according to the present invention will be described hereinbelow.

The image processing apparatus 130 according to this example has a plurality of at least one of a threshold value of brightness value and a predetermined number of voxels, and the user can select the threshold value or the predetermined number via the input unit.

It is assumed that the image processing apparatus 130 stores a plurality of threshold values in a main storage device. It is assumed that the image processing apparatus 130 stores a first threshold value and a second threshold value, which is lower than the first threshold value, in the main storage device with respect to the brightness value of a voxel.

Figure 15:
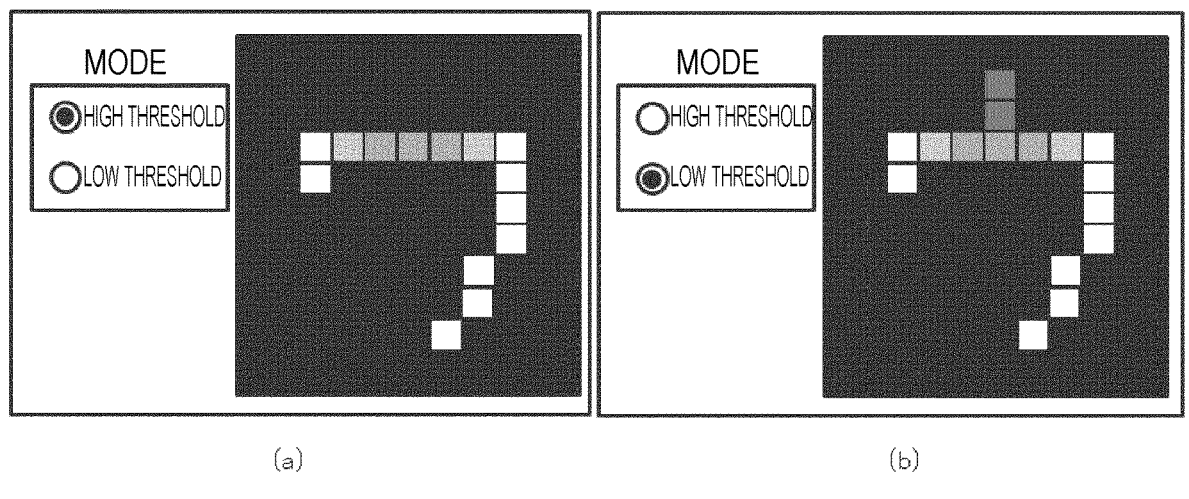
FIG. 15 is a figure showing an example of a display screen according to Example 6.

As shown in (a) of FIG. 15, the image processing apparatus 130 displays a display mode selection means together with a projection image on the display unit 136. Here, "high threshold value" and "low threshold value" can be exclusively selected with a radio button. In FIG. 15, (a) shows a state in which "high threshold value" is selected, and voxels having a threshold value larger than the first threshold value are coordinate-converted to pixel coordinates constituting the projection plane. The user can select one of the modes via the input unit 135.

In FIG. 15, (b) shows an example of a display screen when "low threshold value" is selected. In this example, since the second threshold value is used, it is understood that voxels with a brightness value lower than that in (a) of FIG. 15 are associated with the projection plane. Typically, when "low threshold value" is selected, voxels are associated with more pixels than when "high threshold value" is selected.

Further, the image processing apparatus 130 displays a plurality of images, which have been subjected to the coordinate conversion processing based on different threshold values, side by side on the same screen. When the user selects one image, the image processing apparatus enlarges and displays the selected image, or the display of the image not selected may be ended.

In the present example, the mode in which the user can select a threshold value has been described, but it is also possible for the user to select the number of pixels associated with the voxels among the pixels on the projection plane.

According to the present example, since the user can switch the threshold value, it is possible to observe the projection image suitable for the purpose.

(8) Example 7

Still another example of the present invention will be described hereinbelow with reference to FIG. 16.

Figure 16:
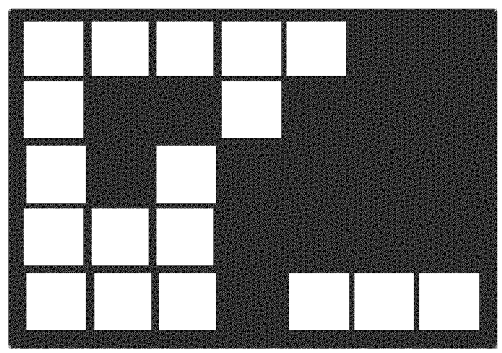
FIG. 16 is a figure showing an example of a display screen according to Example 7.
Figure 16:
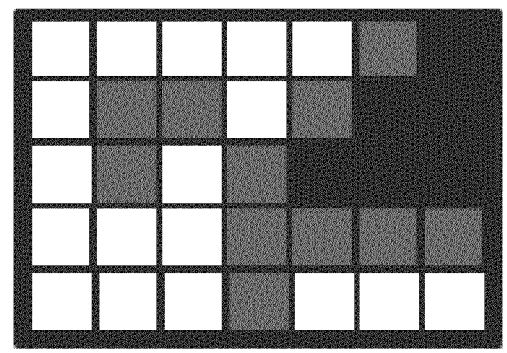

In FIG. 16, (a) shows an example of an image of a certain projection plane. In this figure, a white cell indicates a pixel having an associated voxel, and a black cell indicates a pixel having no associated voxel. For simplicity of explanation, it is assumed that the white cell has the maximum brightness value in the three-dimensional volume data 111.

As shown in (a) of FIG. 16, where the difference in brightness value between a pixel having no associated voxel and a pixel adjacent thereto is large, the boundary thereof is emphasized. As a result, the user may feel discomfort.

Therefore, in the present example, in the case where a pixel associated with a voxel by the coordinate conversion processing is adjacent to a pixel having no associated voxel, the image processing apparatus 130 performs processing of interpolating the brightness values of the pixels having no associated voxels, for example, by using the brightness values of surrounding pixels. As a result, it is possible to make the boundary appear smooth as shown in (b) of FIG. 16.

(9) Other Examples

In the examples described above, the case is explained in which the voxel coordinate data storage unit 132 stores the voxel coordinate data 133 corresponding to all the voxels constituting the three-dimensional space. However, when the range of the number of voxels or the brightness value to be used for rendering the maximum intensity projection image is determined, the voxel coordinate data storage unit may store only the voxel coordinate data 133 of the number of voxels satisfying the condition or the number satisfying the range of the brightness value.

In the example described above, it is assumed that the three-dimensional volume data 111 are photoacoustic imaging data, and the case is explained in which the ratio of the number of voxels used for rendering the maximum intensity projection image is 10% of the total number of voxels. However, optimum values may be used for these threshold values in accordance with the type of three-dimensional image data used as the three-dimensional volume data 111 and the distribution of brightness values.

In the above-described examples, the case is explained in which the coordinate conversion processing by the coordinate conversion unit 134 and the rendering are executed in two stages, but only the first stage described above may be executed. When such a mode is used, the image quality of the maximum intensity projection image still does not change significantly.

In the above-described examples, when a plurality of voxels is associated with the same pixel, the brightness value of the voxel having the largest brightness value is displayed, but in the case of brightness values of a group of high-brightness voxels (voxels with a brightness value higher than a predetermined threshold value, or up to a predetermined number of voxels in order from a voxel having a largest brightness value), it is not necessary to be limited to the largest brightness value. This is because where the voxels belong to the group of high-brightness voxels, the difference in brightness is small, and the difference in brightness cannot be visually recognized or the difference in brightness is negligibly small.

In this display method, for example, when two voxels belonging to the group of high-brightness voxels are associated with one pixel, it means that the brightness value of the voxel with lower brightness may be displayed. For example, in the case of voxels of the group of high-brightness voxel, this display method can be realized by associating the brightness of the newly associated voxel, regardless of whether or not another voxel has already been associated with the associated pixel. Even when this method is adopted, there is no substantial effect on visual image quality and processing speed.

In the above example, the case is explained in which rendering of the maximum intensity projection image corresponding to the designated rotation angle is executed with respect to the aforementioned group of high-brightness voxels on the condition that the positional relationship between the three-dimensional volume data 111 and the projection plane 140 inputted through the input unit 135 is received, and thereafter the rendering of the maximum intensity projection image is continued for the group of low-brightness voxels. However, when an automatic rotation function with a finite number of rotations is loaded into the image processing system 100, the rendering processing operation of the maximum intensity projection image by the group of high-brightness voxels may be used. With the automatic rotation function, it is assumed that the direction of rotation and amount of rotation to be used in each rotation are determined in advance. After completion of the rendering processing of the maximum intensity projection image in accordance with the automatic rotation, the processing of raising the rendering quality by using the group of low-brightness voxels may be executed in the same manner as in the above-described examples.

In the above-described examples, the change of the observation direction has been explained by way of example, but similar processing can be also applied to enlargement or reduction of the image unless otherwise specified.

In the above-described examples, the case is explained in which conversion to the coordinate values of pixels on the projection plane is performed with respect to voxels having a brightness value higher than a predetermined threshold value, or with respect to up to a predetermined number of voxels in order from a voxel having a largest brightness value. However, the present invention is not limited to such processing, and conversion of coordinate values may be also performed with respect to voxels having a brightness value in a predetermined range, or with respect to a predetermined number of voxels. For example, in the case where the maximum brightness value and the brightness value in the vicinity thereof, in the three-dimensional voxel data, are components caused by noise, where the projection onto the projection plane is performed including the maximum brightness value, it can cause a reduction in visibility. Therefore, voxels included in the range of brightness values excluding the maximum brightness value may be set as the objects to be projected.

A maximum intensity projection image is rendered by extracting, as objects to be rendered, only voxels having a high brightness value among voxels constituting three-dimensional volume data and using the brightness values of these voxels for the corresponding pixels. According to this method, even when the maximum intensity projection image is rotationally displayed, the maximum intensity projection image of high image quality can be rendered in a short time.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus comprising:
a voxel coordinate data generation unit configured to generate voxel coordinate data in which respective brightness values are associated with coordinate values of respective voxels; and
a coordinate conversion unit configured to convert the coordinate values of voxels to coordinate values of corresponding pixels on a projection plane at least with respect to a predetermined number of voxels in order from a voxel having a largest brightness value, and to execute rendering processing of a projection image by using brightness values of the corresponding voxels for the pixels obtained by the conversion,
wherein the voxel coordinate data generation unit and the coordinate conversion unit are implemented by at least one processor of the image processing apparatus.

2. The image processing apparatus according to claim 1, wherein in a case more than one voxel corresponds to a coordinate value of the same pixel, the coordinate conversion unit uses a voxel having a higher brightness value, or the brightness value of a voxel having a larger brightness value.

3. The image processing apparatus according to claim 1, wherein the coordinate conversion unit (1) executes, in advance, processing of rearranging the voxel coordinate data in order of magnitude of the brightness values or in approximate order of magnitude of the brightness values, and (2) calculates coordinate values of the corresponding pixel in units of one or a plurality of voxels in order from a voxel having a higher brightness value, and executes rendering processing of a projection image by using the brightness value of the corresponding voxel for the pixel with the calculated coordinate values.

4. The image processing apparatus according to claim 1, wherein after finishing rendering processing using, as objects to be processed, only a predetermined number of voxels in order from a voxel having a largest brightness value, the coordinate conversion unit executes rendering processing using brightness values of remaining voxels.

5. The image processing apparatus according to claim 1, wherein when an enlarged display of the projection plane is instructed, the coordinate conversion unit executes rendering processing to linearly interpolate a partial region of the projection plane according to an enlargement ratio and to display the enlarged partial region.

6. The image processing apparatus according to claim 1, wherein when a reduced display of the projection plane is instructed, the coordinate conversion unit executes rendering processing of a projection image by using the brightness value of the voxel subjected to the coordinate conversion for each pixel on the projection plane reduced according to a reduction ratio.

7. An image processing apparatus comprising:
a voxel coordinate data generation unit configured to generate voxel coordinate data in which coordinate values of one or a plurality of voxels having a brightness value of the same magnitude are associated with each brightness value; and
a coordinate conversion unit configured to convert the coordinate values of voxels to coordinate values of corresponding pixels on a projection plane at least with respect to a predetermined number of voxels in order from a voxel having a largest brightness value, and to execute rendering processing of a projection image by using brightness values of the corresponding voxels for the pixels obtained by the conversion,
wherein the voxel coordinate data generation unit and the coordinate conversion unit are implemented by at least one processor of the image processing apparatus.

8. The image processing apparatus according to claim 7, wherein the coordinate conversion unit calculates coordinate values of the corresponding pixels in units of one or a plurality of voxels in order from a voxel having a higher brightness value, and uses and executes rendering processing of a projection image by using the brightness value of the corresponding voxels for the pixels with the calculated coordinate values.

9. The image processing apparatus according to claim 7, wherein after finishing rendering processing using, as objects to be processed, only a predetermined number of voxels in order from a voxel having a largest brightness value, the coordinate conversion unit executes rendering processing using brightness values of remaining voxels.

10. The image processing apparatus according to claim 7, wherein when an enlarged display of the projection plane is instructed, the coordinate conversion unit executes rendering processing to linearly interpolate a partial region of the projection plane according to an enlargement ratio and to display the enlarged partial region.

11. An image processing method comprising:
a voxel coordinate data generation step of generating voxel coordinate data in which respective brightness values are associated with coordinate values of respective voxels;
a coordinate value conversion step of converting the coordinate values of voxels to coordinate values of corresponding pixels on a projection plane at least with respect to a predetermined number of voxels in order from a voxel having a largest brightness value; and
a brightness display step of executing rendering processing of a projection image by using brightness values of the corresponding voxels for the pixels obtained by the conversion.

12. The image processing method according to claim 11, further comprising a rearrangement step of executing processing of rearranging the voxel coordinate data in order of magnitude of the brightness values or in approximate order of magnitude of the brightness values,
wherein, in the coordinate value conversion step, coordinate values of the corresponding pixels are calculated in units of one or a plurality of voxels in order from voxel coordinate data having a high brightness value, and wherein, in the brightness display step, the brightness value of the corresponding voxels are used and displayed for the pixels with the calculated coordinate values.

13. A non-transitory computer-readable storing medium storing an image processing program that causes a computer of an image processing apparatus for rendering a projection image based on three-dimensional volume data on a display unit to execute:
- a voxel coordinate data generation step of generating voxel coordinate data in which respective brightness values are associated with coordinate values of respective voxels constituting the three-dimensional volume data;
- a coordinate value conversion step of converting the coordinate values of voxels to coordinate values of corresponding pixels on a projection plane at least with respect to a predetermined number of voxels in order from a voxel having a largest brightness value; and
- a brightness display step of executing rendering processing of a projection image by using brightness values of the corresponding voxels for the pixels obtained by the conversion.

14. The non-transitory computer-readable storing medium according to claim 13, the image processing program further causing the computer to execute a rearrangement step of executing processing of rearranging the voxel coordinate data in order of magnitude of the brightness values or in approximate order of magnitude of the brightness values,
wherein, in the coordinate value conversion step, the computer is caused to execute a step of calculating coordinate values of the corresponding pixels in units of one or a plurality of voxels in order from voxel coordinate data having a high brightness value, and
wherein, in the brightness display step, the computer is caused to execute a step of using and displaying the brightness values of the corresponding voxels for the pixels with the calculated coordinate values.

15. An image processing system for rendering a projection image based on three-dimensional volume data on a display unit, the image processing system comprising:
- a server that stores the three-dimensional volume data;
- an image processing apparatus; and
- a network that connects the server and the image processing apparatus,
wherein the image processing apparatus includes:
  (1) a voxel coordinate data generation unit configured to generate voxel coordinate data in which respective brightness values are associated with coordinate values of respective voxels constituting the three-dimensional volume data; and
  (2) a coordinate conversion unit configured to convert the coordinate values of voxels to coordinate values of corresponding pixels on a projection plane at least with respect to a predetermined number of voxels in order from a voxel having a largest brightness value, and to execute rendering processing of a projection image by using brightness values of the corresponding voxels for the pixels obtained by the conversion,
wherein the voxel coordinate data generation unit and the coordinate conversion unit are implemented by at least one processor of the image processing apparatus.

16. An image processing apparatus comprising:
an input unit configured to receive an instruction inputted by user;
a voxel coordinate data generation unit configured to generate voxel coordinate data in which respective brightness values are associated with coordinate values of respective voxels; and
a coordinate conversion unit configured to convert the coordinate values of voxels to coordinate values of corresponding pixels on a projection plane, and to execute rendering processing of a projection image by using brightness values of the corresponding voxels for the pixels obtained by the conversion,
wherein the voxel coordinate data generation unit and the coordinate conversion unit are implemented by at least one processor of the image processing apparatus, and
wherein in a case where the input unit receives the instruction to change an observation direction, the coordinate conversion unit reduces the number of voxels for the conversion.

17. The image processing apparatus according to claim 16, wherein in the case where the input unit receives the instruction to change the observation direction, the coordinate conversion unit converts the coordinate values at least with respect to a predetermined number of voxels in order from a voxel having a largest brightness value.

18. The image processing apparatus according to claim 16, wherein in the case where the input unit does not receive the instruction to change the observation direction, the coordinate conversion unit converts the coordinate values of all the voxels.

19. The image processing apparatus according to claim 16, wherein in the case where the input unit receives the instruction to change an observation direction, the coordinate conversion unit reduces the number of voxels with the brightness values to be used for the pixels of the projection image.

* * * * *